(12) United States Patent
Davis et al.

(10) Patent No.: US 7,914,466 B2
(45) Date of Patent: Mar. 29, 2011

(54) MEDICAL DEVICE WITH COLLAPSE-RESISTANT LINER AND METHOD OF MAKING SAME

(75) Inventors: Clark C. Davis, Holladay, UT (US); Kevin T. Olson, Salt Lake City, UT (US); Dewayne C. Fox, South Jordan, UT (US)

(73) Assignee: Precision Vascular Systems, Inc., West Valley City, UT (US)

( * ) Notice: Subject to any disclaimer, the term of this patent is extended or adjusted under 35 U.S.C. 154(b) by 1504 days.

(21) Appl. No.: 10/523,709

(22) PCT Filed: Aug. 5, 2003

(86) PCT No.: PCT/US03/24604
§ 371 (c)(1),
(2), (4) Date: Dec. 14, 2005

(87) PCT Pub. No.: WO2004/012804
PCT Pub. Date: Feb. 12, 2004

(65) Prior Publication Data
US 2006/0189896 A1 Aug. 24, 2006

Related U.S. Application Data

(63) Continuation-in-part of application No. 10/213,123, filed on Aug. 5, 2002.

(51) Int. Cl.
*A61M 25/00* (2006.01)
(52) U.S. Cl. ...................................................... 600/585
(58) Field of Classification Search .................. 600/433, 600/434, 585; 604/164.13
See application file for complete search history.

(56) References Cited

U.S. PATENT DOCUMENTS
1,553,227 A 9/1925 Feyk et al.
(Continued)

FOREIGN PATENT DOCUMENTS
AU 723040 12/1997
(Continued)

OTHER PUBLICATIONS
5,135,131, Aug. 4, 1992, Shiber.
(Continued)

*Primary Examiner* — Max Hindenburg
*Assistant Examiner* — Jonathan M. Foreman
(74) *Attorney, Agent, or Firm* — Seager, Tufte & Wickhem, LLC

(57) ABSTRACT

A medical device for guiding through anatomy, such as a catheter or guidewire, with a tubular body that has been slotted to enhance bending flexibility, and a polymer liner with an anti-collapsing structure, and a method of making a medical device with a kink-resistant corrugated tubular member and an anti-collapsing structure. Anti collapsing structures may be helical or annular, and may be wire, such as ribbon wire, grooves in the liner, corrugations, or a braid. Liners may be bonded to the anti-collapsing structure, or may have two layers, with the anti-collapsing structure between the layers. Corrugations may be formed between sections of the anti-collapsing structure with heat, pressure, stretching, compression, a mold, or a combination thereof, and may extend inward or outward. Shape or wall thickness may vary along the length to provide a varying bending stiffness. Slots may be formed in groups of two, three, or more, and adjacent groups may be rotated about the axis forming a helical pattern.

15 Claims, 14 Drawing Sheets

U.S. PATENT DOCUMENTS

| | | |
|---|---|---|
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,698,890 A * | 10/1987 | Neaves ............... 29/412 |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,358,493 A | 10/1994 | Schweich et al. |
| 5,365,942 A | 11/1994 | Shank |
| 5,365,943 A | 11/1994 | Jansen |
| 5,368,564 A | 11/1994 | Savage |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |

| | | | | | | |
|---|---|---|---|---|---|---|
| 5,571,073 A | 11/1996 | Castillo | | 6,171,296 B1 | 1/2001 | Chow |
| 5,573,520 A | 11/1996 | Schwartz et al. | | 6,183,410 B1 | 2/2001 | Jacobsen et al. |
| 5,584,821 A | 12/1996 | Hobbs et al. | | 6,193,686 B1 | 2/2001 | Estrada et al. |
| 5,599,326 A | 2/1997 | Carter | | 6,197,014 B1 | 3/2001 | Samson et al. |
| 5,599,492 A | 2/1997 | Engelson | | 6,203,485 B1 | 3/2001 | Urick |
| 5,601,539 A | 2/1997 | Corso, Jr. | | 6,214,042 B1 | 4/2001 | Jacobsen et al. |
| 5,605,162 A | 2/1997 | Mirzaee et al. | | 6,228,073 B1 | 5/2001 | Noone et al. |
| 5,622,184 A | 4/1997 | Ashby et al. | | 6,248,082 B1 | 6/2001 | Jafari |
| 5,630,806 A | 5/1997 | Inagaki et al. | | 6,251,092 B1 | 6/2001 | Qin et al. |
| 5,637,089 A | 6/1997 | Abrams et al. | | 6,254,549 B1 | 7/2001 | Ramzipoor |
| 5,656,011 A | 8/1997 | Uihlein et al. | | 6,260,458 B1 | 7/2001 | Jacobsen et al. |
| 5,658,264 A | 8/1997 | Samson et al. | | 6,273,404 B1 | 8/2001 | Holman et al. |
| 5,666,968 A | 9/1997 | Imran et al. | | 6,273,876 B1 | 8/2001 | Klima et al. |
| 5,666,969 A | 9/1997 | Urick et al. | | 6,290,656 B1 | 9/2001 | Boyle et al. |
| 5,669,926 A | 9/1997 | Aust et al. | | 6,296,616 B1 | 10/2001 | McMahon |
| 5,676,659 A | 10/1997 | McGurk | | 6,296,631 B2 | 10/2001 | Chow |
| 5,676,697 A | 10/1997 | McDonald | | 6,302,870 B1 | 10/2001 | Jacobsen et al. |
| 5,682,894 A | 11/1997 | Orr et al. | | 6,325,790 B1 | 12/2001 | Trotta |
| 5,690,120 A | 11/1997 | Jacobsen et al. | | 6,338,725 B1 | 1/2002 | Hermann et al. |
| 5,720,300 A | 2/1998 | Fagan et al. | | 6,346,091 B1 | 2/2002 | Jacobsen et al. |
| 5,722,609 A | 3/1998 | Murakami | | 6,352,515 B1 | 3/2002 | Anderson et al. |
| 5,728,063 A | 3/1998 | Preissman et al. | | 6,355,005 B1 | 3/2002 | Powell et al. |
| 5,741,429 A | 4/1998 | Donadio, III et al. | | 6,355,027 B1 | 3/2002 | Le et al. |
| 5,746,701 A | 5/1998 | Noone | | 6,368,315 B1 | 4/2002 | Gillis et al. |
| 5,769,830 A | 6/1998 | Parker | | 6,368,316 B1 | 4/2002 | Jansen et al. |
| 5,772,609 A | 6/1998 | Nguyen et al. | | 6,375,628 B1 | 4/2002 | Zadno-Azizi et al. |
| 5,782,809 A | 7/1998 | Umeno et al. | | 6,375,774 B1 | 4/2002 | Lunn et al. |
| 5,788,653 A | 8/1998 | Lorenzo | | 6,379,369 B1 | 4/2002 | Abrams et al. |
| 5,788,654 A | 8/1998 | Schwager | | 6,390,993 B1 | 5/2002 | Cornish et al. |
| 5,788,707 A | 8/1998 | Del Toro et al. | | 6,398,758 B1 | 6/2002 | Jacobsen et al. |
| 5,792,116 A * | 8/1998 | Berg et al. ............... 604/202 | | 6,428,489 B1 | 8/2002 | Jacobsen et al. |
| 5,792,124 A | 8/1998 | Horrigan et al. | | 6,428,512 B1 | 8/2002 | Anderson et al. |
| 5,797,856 A | 8/1998 | Frisbie et al. | | 6,431,039 B1 | 8/2002 | Jacobsen et al. |
| 5,800,454 A | 9/1998 | Jacobsen et al. | | 6,440,088 B1 | 8/2002 | Jacobsen |
| 5,807,075 A | 9/1998 | Jacobsen et al. | | 6,478,778 B1 | 11/2002 | Jacobsen et al. |
| 5,807,249 A | 9/1998 | Qin et al. | | 6,491,648 B1 | 12/2002 | Cornish et al. |
| 5,810,885 A | 9/1998 | Zinger | | 6,491,671 B1 | 12/2002 | Larson, III et al. |
| 5,813,996 A | 9/1998 | St. Germain et al. | | 6,503,244 B2 | 1/2003 | Hayman |
| 5,827,225 A | 10/1998 | Ma Schwab | | 6,508,803 B1 | 1/2003 | Horikawa et al. |
| 5,827,242 A | 10/1998 | Follmer et al. | | 6,524,301 B1 | 2/2003 | Wilson et al. |
| 5,833,632 A | 11/1998 | Jacobsen et al. | | 6,530,934 B1 | 3/2003 | Jacobsen et al. |
| 5,836,926 A | 11/1998 | Peterson et al. | | 6,547,779 B2 | 4/2003 | Levine et al. |
| 5,843,050 A | 12/1998 | Jones et al. | | 6,553,880 B2 | 4/2003 | Jacobsen et al. |
| 5,843,244 A | 12/1998 | Pelton et al. | | 6,556,873 B1 | 4/2003 | Smits |
| 5,851,203 A | 12/1998 | van Muiden | | 6,579,246 B2 | 6/2003 | Jacobsen et al. |
| 5,895,378 A | 4/1999 | Nita | | 6,602,280 B2 | 8/2003 | Chobotov |
| 5,897,537 A | 4/1999 | Berg et al. | | 6,610,046 B1 | 8/2003 | Usami et al. |
| 5,902,254 A | 5/1999 | Magram | | 6,623,448 B2 | 9/2003 | Slater |
| 5,902,290 A | 5/1999 | Peacock, III et al. | | 6,636,758 B2 | 10/2003 | Sanchez et al. |
| 5,904,657 A | 5/1999 | Unsworth et al. | | 6,638,266 B2 | 10/2003 | Wilson et al. |
| 5,906,618 A | 5/1999 | Larson, III | | 6,652,508 B2 | 11/2003 | Griffin et al. |
| 5,911,715 A | 6/1999 | Berg et al. | | 6,682,493 B2 | 1/2004 | Mirigian |
| 5,911,717 A | 6/1999 | Jacobsen et al. | | 6,712,826 B2 | 3/2004 | Lui |
| 5,916,177 A | 6/1999 | Schwager | | 6,749,560 B1 | 6/2004 | Konstorum et al. |
| 5,916,178 A | 6/1999 | Noone | | 6,766,720 B1 | 7/2004 | Jacobsen et al. |
| 5,916,194 A | 6/1999 | Jacobsen et al. | | 6,777,644 B2 | 8/2004 | Peacock, III et al. |
| 5,931,830 A | 8/1999 | Jacobsen et al. | | 6,811,544 B2 | 11/2004 | Schaer |
| 5,935,108 A | 8/1999 | Katoh et al. | | 6,837,898 B2 | 1/2005 | Boyle et al. |
| 5,951,539 A | 9/1999 | Nita et al. | | 6,866,642 B2 | 3/2005 | Kellerman et al. |
| 5,971,975 A | 10/1999 | Mills et al. | | 6,887,235 B2 | 5/2005 | O'Connor et al. |
| 6,001,068 A | 12/1999 | Uchino et al. | | 7,001,369 B2 | 2/2006 | Griffin et al. |
| 6,004,279 A | 12/1999 | Crowley et al. | | 7,074,197 B2 | 7/2006 | Reynolds et al. |
| 6,014,919 A | 1/2000 | Jacobsen et al. | | 2002/0013540 A1 | 1/2002 | Jacobsen et al. |
| 6,017,319 A | 1/2000 | Jacobsen et al. | | 2002/0019599 A1 | 2/2002 | Rooney et al. |
| 6,022,343 A | 2/2000 | Johnson et al. | | 2002/0082499 A1 | 6/2002 | Jacobsen et al. |
| 6,022,369 A | 2/2000 | Jacobsen et al. | | 2002/0198492 A1* | 12/2002 | Miller et al. ............. 604/96.01 |
| 6,024,730 A | 2/2000 | Pagan | | 2003/0009208 A1 | 1/2003 | Snyder et al. |
| 6,027,461 A | 2/2000 | Walker et al. | | 2003/0060732 A1 | 3/2003 | Jacobsen et al. |
| 6,042,553 A | 3/2000 | Solar et al. | | 2003/0069520 A1 | 4/2003 | Skujins et al. |
| 6,045,547 A | 4/2000 | Ren et al. | | 2003/0069521 A1 | 4/2003 | Reynolds et al. |
| 6,048,339 A | 4/2000 | Zirps et al. | | 2003/0069522 A1 | 4/2003 | Jacobsen et al. |
| 6,056,702 A | 5/2000 | Lorenzo | | 2003/0093059 A1 | 5/2003 | Griffin et al. |
| 6,063,101 A | 5/2000 | Jacobsen et al. | | 2003/0105415 A1 | 6/2003 | Mirigian |
| 6,063,200 A | 5/2000 | Jacobsen et al. | | 2004/0002713 A1 | 1/2004 | Olson, Jr. et al. |
| 6,066,361 A | 5/2000 | Jacobsen et al. | | 2004/0167437 A1 | 8/2004 | Sharrow et al. |
| 6,106,485 A | 8/2000 | McMahon | | 2004/0181174 A2 | 9/2004 | Davis et al. |
| 6,106,488 A | 8/2000 | Fleming et al. | | 2004/0181176 A1 | 9/2004 | Jafari et al. |
| 6,139,510 A | 10/2000 | Palermo | | 2006/0264904 A1 | 11/2006 | Kerby et al. |
| 6,165,292 A | 12/2000 | Abrams et al. | | 2008/0021347 A1 | 1/2008 | Jacobsen et al. |

| | | | |
|---|---|---|---|
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021404 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |
| 2008/0077119 A1 | 3/2008 | Snyder et al. |

FOREIGN PATENT DOCUMENTS

| | | |
|---|---|---|
| AU | 733966 | 4/1998 |
| BR | PI 9712829-5 | 1/2000 |
| CA | 2266685 | 5/2006 |
| CN | 1230914 | 10/1999 |
| DE | 25 39 191 | 3/1976 |
| DE | 285514 | 12/1990 |
| EP | 0 045 931 | 2/1982 |
| EP | 0 069 522 | 1/1983 |
| EP | 0 087 933 | 9/1983 |
| EP | 0 111 044 | 6/1984 |
| EP | 0377453 | 7/1990 |
| EP | 0 181 174 | 1/1991 |
| EP | 0 521 595 | 1/1993 |
| EP | 0 608 853 | 8/1994 |
| EP | 0 565 065 | 6/1996 |
| EP | 0 778 038 | 6/1997 |
| EP | 0 778 039 | 6/1997 |
| EP | 0 778 040 | 6/1997 |
| EP | 0 790 066 | 8/1997 |
| EP | 0 812 599 | 12/1997 |
| EP | 0 865 773 | 9/1998 |
| EP | 0 917 885 | 5/1999 |
| EP | 0 935 947 | 8/1999 |
| EP | 0 937 481 | 8/1999 |
| EP | 0 934 141 | 11/2005 |
| GB | 2214354 | 8/1989 |
| GB | 2257269 | 1/1993 |
| JP | 588522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 6393516 | 4/1988 |
| JP | 63-181774 A | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 3081831 | 4/1991 |
| JP | 03-122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5-506806 | 10/1993 |
| JP | 5-507857 | 11/1993 |
| JP | 5309519 | 11/1993 |
| JP | 6-501179 A | 2/1994 |
| JP | 631749 | 4/1994 |
| JP | 6169996 | 6/1994 |
| JP | 663224 | 9/1994 |
| JP | 6312313 | 11/1994 |
| JP | 7-28562 U | 1/1995 |
| JP | 7-51067 Y2 | 2/1995 |
| JP | 728562 | 5/1995 |
| JP | 7124164 | 5/1995 |
| JP | 7124263 | 5/1995 |
| JP | 7136280 | 5/1995 |
| JP | 7148264 | 6/1995 |
| JP | 7505561 | 6/1995 |
| JP | 7037199 | 7/1995 |
| JP | 7185009 | 7/1995 |
| JP | 7255855 | 10/1995 |
| JP | 7275366 | 10/1995 |
| JP | 751067 | 11/1995 |
| JP | 8229888 | 9/1996 |
| JP | 8509141 | 10/1996 |
| JP | 8317988 | 12/1996 |
| JP | 9000164 | 4/1997 |
| JP | 9-276413 A | 10/1997 |
| JP | 9276413 | 10/1997 |
| JP | 9-294813 A | 11/1997 |
| JP | 9294813 | 11/1997 |
| JP | 10-118193 | 5/1998 |
| JP | 10-305039 | 11/1998 |
| JP | 10-3055039 | 11/1998 |
| JP | 10-328191 A | 12/1998 |
| JP | 10328191 | 12/1998 |
| JP | 11-226131 A | 8/1999 |
| JP | 11-267224 A | 10/1999 |
| JP | 11-276491 A | 10/1999 |
| JP | 2000197704 | 7/2000 |
| JP | 2000-510722 A | 8/2000 |
| JP | 2000-511083 A | 8/2000 |
| JP | 2001-500808 A | 1/2001 |
| JP | 2002-529137 A | 9/2002 |
| JP | 2002-542901 A | 12/2002 |
| JP | 2002-543896 A | 12/2002 |
| JP | 2003-517893 A | 6/2003 |
| JP | 2005-534407 | 11/2005 |
| SU | 712908 | 1/1980 |
| SU | 758421 | 8/1980 |
| SU | 1529365 | 12/1989 |
| WO | WO 90/02520 | 3/1990 |
| WO | WO 91/13364 | 9/1991 |
| WO | WO 92/04072 | 3/1992 |
| WO | WO 92/07619 | 5/1992 |
| WO | WO 93/04722 | 3/1993 |
| WO | WO 93/11313 | 6/1993 |
| WO | WO 95/24236 | 9/1995 |
| WO | WO 96/19255 | 6/1996 |
| WO | WO 97/10022 | 3/1997 |
| WO | WO 97/25914 | 7/1997 |
| WO | WO 97/43949 | 11/1997 |
| WO | WO 97/44083 | 11/1997 |
| WO | WO 97/44086 | 11/1997 |
| WO | WO 98/10694 | 3/1998 |
| WO | 9904847 | 2/1999 |
| WO | WO 99/11313 | 3/1999 |
| WO | WO 00/27303 | 5/2000 |
| WO | WO 00/30710 | 6/2000 |
| WO | WO 00/48645 | 8/2000 |
| WO | WO 00/57943 | 10/2000 |
| WO | WO 00/66199 | 11/2000 |
| WO | WO 00/67845 | 11/2000 |
| WO | WO 00/72907 | 12/2000 |
| WO | WO 01/28620 | 4/2001 |
| WO | 0136034 | 5/2001 |
| WO | 0145912 | 6/2001 |
| WO | WO 01/45773 | 6/2001 |
| WO | WO 01/93920 | 12/2001 |
| WO | WO 02/13682 | 2/2002 |
| WO | WO 02/062540 | 8/2002 |
| WO | WO 03/04086 | 1/2003 |
| WO | WO 03/008148 | 1/2003 |
| WO | WO 2004/012804 | 2/2004 |
| WO | 2004047899 | 6/2004 |

OTHER PUBLICATIONS

"Mechanical Design and Systems Handbook", H.A. Rothbart, 1964, p. 33-13 (one sheet).

\* cited by examiner

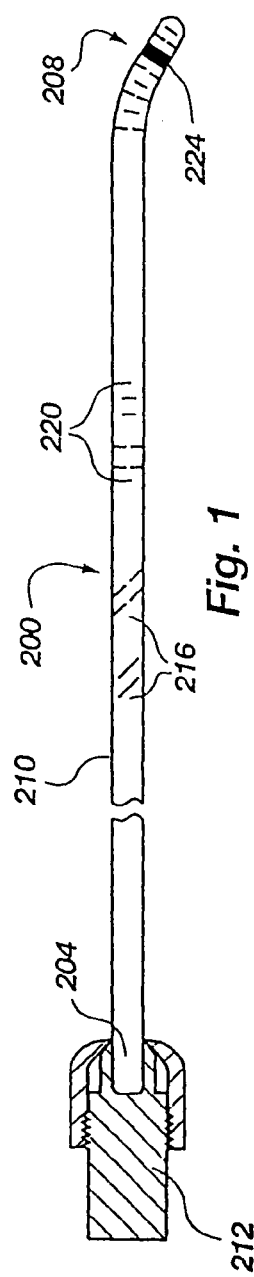
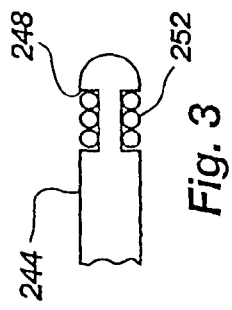
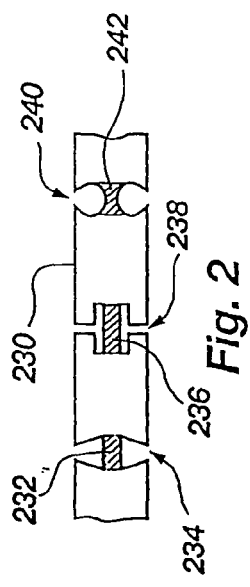
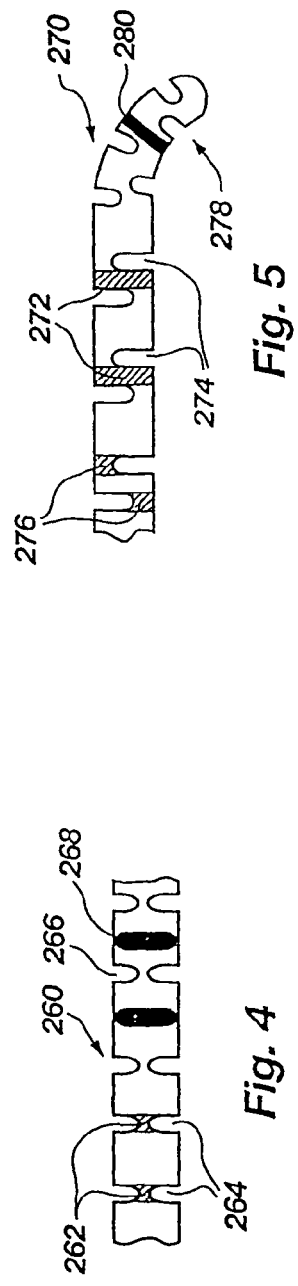
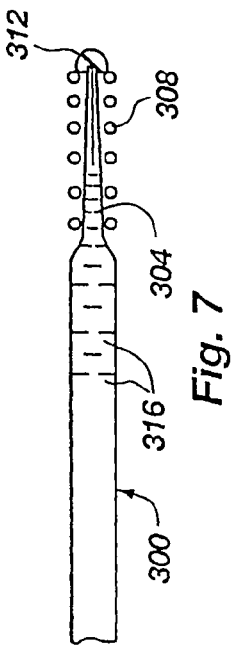
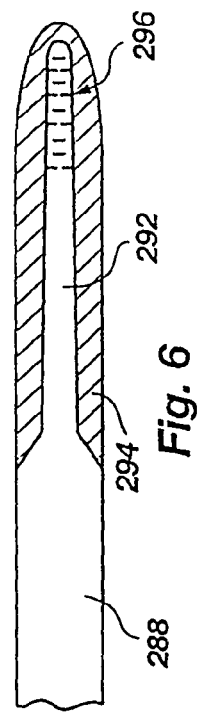

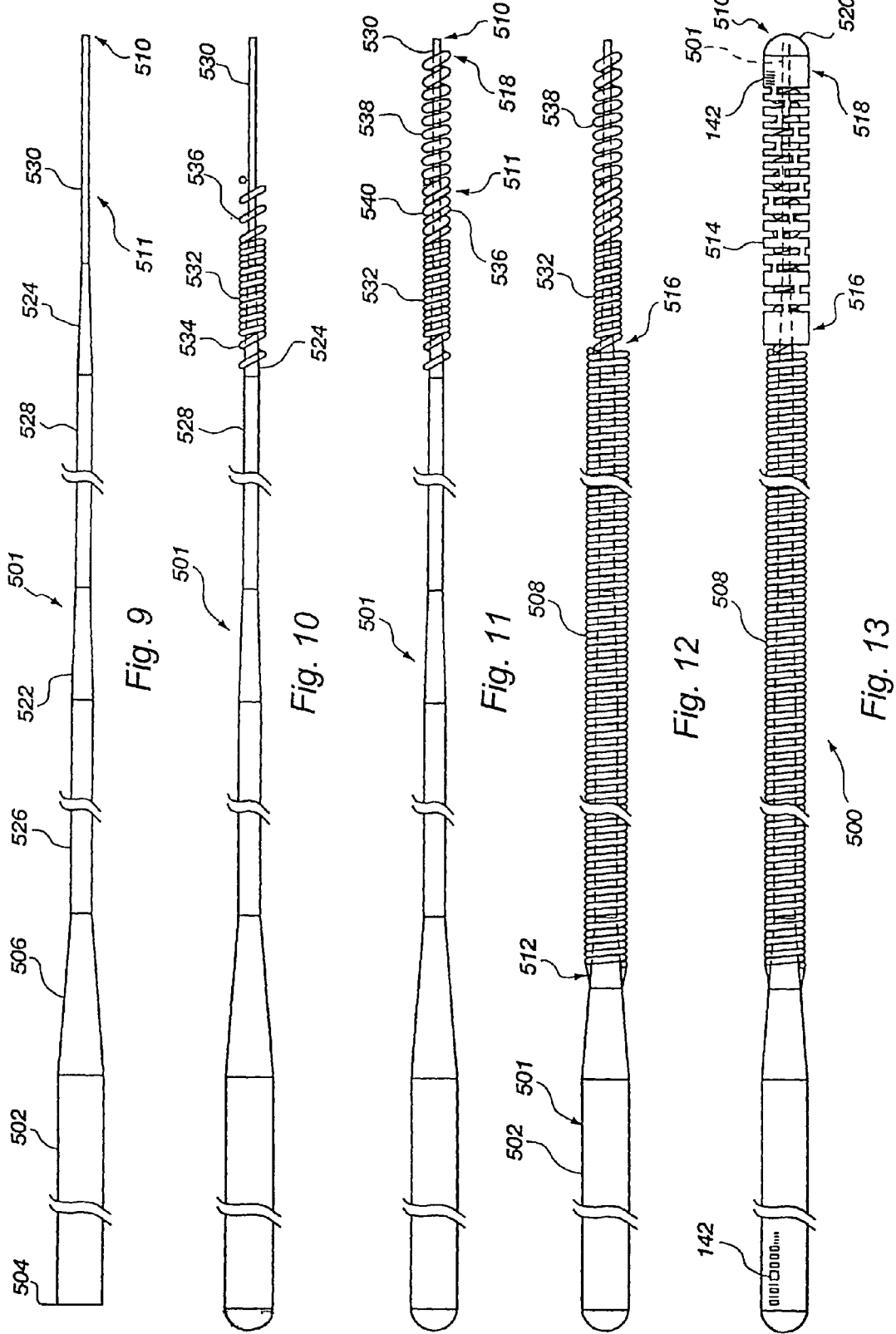

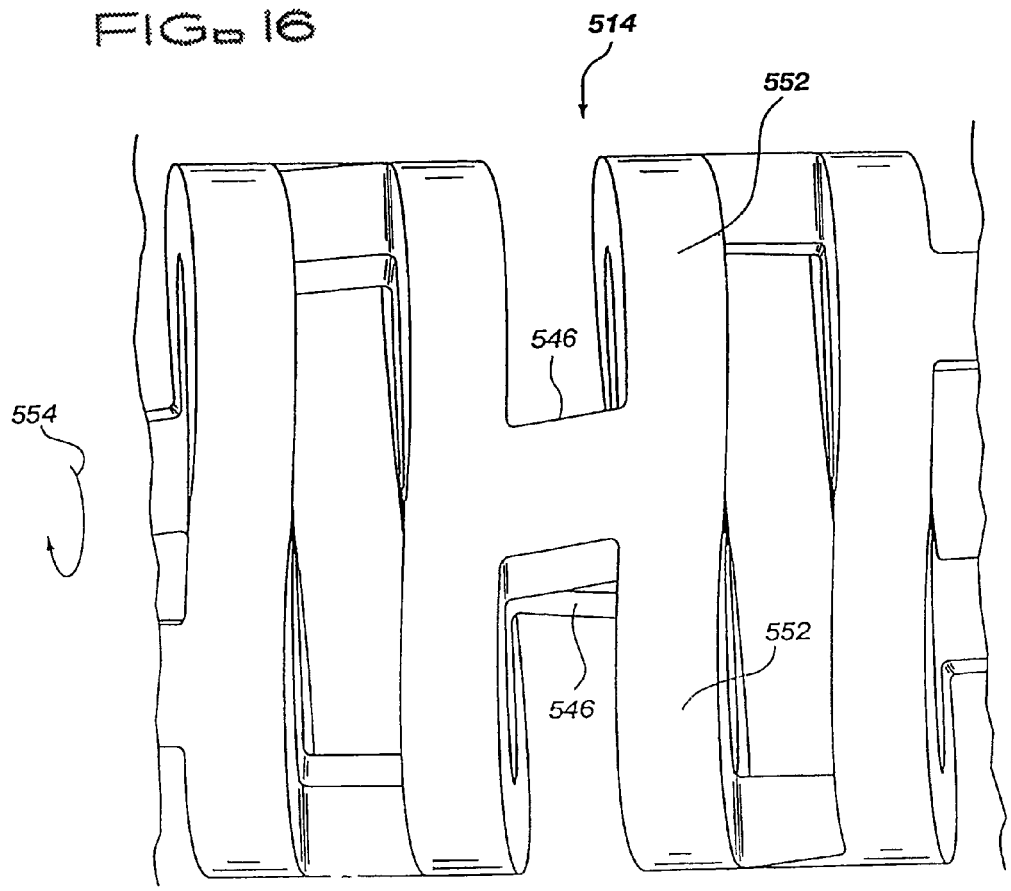
FIG. 16
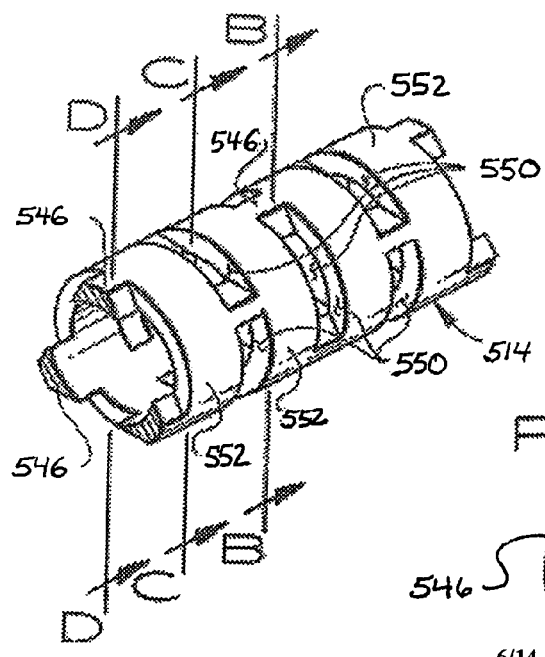
FIG. 16A
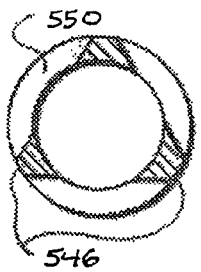
FIG. 16B
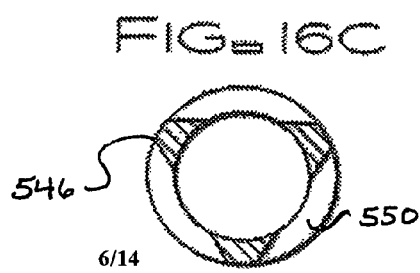
FIG. 16C
FIG. 16D

MEDICAL DEVICE WITH COLLAPSE-RESISTANT LINER AND METHOD OF MAKING SAME

This application is the U.S. National Stage of International Application No. PCT/US0324604 filed Aug. 5, 2003, which is a continuation-in-part of U.S. patent application Ser. No. 10/213,123 filed on Aug. 5, 2002, both of which are incorporated herein by reference. Additionally, this application is a continuation-in-part of U.S. patent application Ser. No. 10/213,123 filed on Aug. 5, 2002.

FIELD OF THE INVENTION

This invention relates to medical devices for use within bodies and methods for making and using such devices. The medical devices may be, for example, catheters, guide wires (guidewires), or hybrids of catheters and guidewires.

BACKGROUND OF THE INVENTION

Catheter guide wires (guidewires) have been used to "lead" or "guide" catheters to desired target locations in animal or human anatomy. This may be done via a body's lumen, for example such as traversing luminal spaces defined by the vasculature to the target location. Typical guidewires may be from about 135 centimeters to 195 centimeters in length, and have been made from two primary components—a stainless steel solid core wire, and a platinum alloy coil spring. The core wire may be tapered on the distal end to increase its flexibility. The coil spring may be soldered to the core wire at its distal end and at a point where the inside diameter of the coil spring matches the outside diameter of the core wire. Platinum has been used for the coil spring because it provides good fluoroscopic or other radiological imaging during navigation of the guidewire in the body, and it is generally biocompatible. The coil spring may also provide softness for the tip of the guidewire to reduce the likelihood of unwanted puncture of a Luminal wall or the damaging of this or other anatomy.

As mentioned, navigation of a guidewire through the anatomy may be achieved with the assistance of radiographic imaging. This may be done by introducing contrast media into the body lumen being traversed and viewing the guidewire in the body lumen using X-ray fluoroscopy or other comparable methods. The guidewire may be provided with a tip that is curved or bent to a desired angle so as to deviate laterally a short distance. By rotation of the wire, the tip can be made to deviate in a selected direction from an axis of the guidewire about which it rotates. In some devices the catheter enables introduction of contrast media at the location of the distal tip to enable the visualization of a Luminal space being traversed by the catheter and guidewire. Visualization may be by fluoroscope, for example, or another device.

The guidewire or catheter may be introduced into a Luminal space, comprising for example a vessel or duct, and advanced therethrough until the guidewire tip reaches a desired vessel or luminal branch. The user may then twist the proximal end of the guidewire so as to rotate and point the curved distal tip into the desired branch so that the device may be advanced farther into the anatomy via the luminal branch. The catheter may be advanced over the guidewire to follow or track the wire. This procedure may be repeated as needed to guide the wire and overlying catheter to the desired target location. Once the catheter has been advanced to the desired location, the guidewire may be withdrawn, depending upon the therapy to be performed. Oftentimes, such as in the case of balloon angioplasty, the guidewire may be left in place during the procedure and may be used to exchange catheters.

From this description, it will be apparent that a guidewire having very low resistance to flexure yet relatively high torsional strength may be most desirable. As the guidewire is advanced into the anatomy, internal resistance from the typically numerous turns, and surface contact, decreases the ability to advance the guidewire further. This, in turn, may lead to a more difficult and prolonged procedure, or, more seriously, failure to access the desired anatomy and thus a failed procedure. A guidewire with high flexibility helps overcome the problems created by internal resistance. However, if the guidewire does not also have good torque characteristics (torsional stiffness), the user will not be able to rotate the distal tip of the guidewire as required by twisting the proximal end. Prior art catheter guidewires that are flexible in bending typically have very poor torsion transmission characteristics or torsional stiffness. The result may be that the end of the guidewire flops around, but cannot easily be turned or rotated within a catheter or vessel.

SUMMARY OF THE INVENTION

The present invention provides medical devices including intravascular devices such as catheters and guidewires. Features of various embodiments of the present invention include that the devices provide the desired flexibility in bending, provide excellent stiffness in torsion, reduce friction with the anatomy, provide adequate radiopacity, particularly at the distal end, resist fatigue, minimize trauma to the patient's anatomy, are capable of navigating through tortuous vasculature, provide the necessary tensile strength to assure complete removal of the medical device, and are inexpensive to manufacture.

In specific embodiments, the present invention provides medical devices having tubular members or liners with anti-collapsing structures that may allow these liners to have thin walls and yet resist collapsing or kinking. These liners may, for example, block or seal some or all of the slots formed in a slotted tubular body that may be concentric with the liner. The present invention also provides various methods of making such medical devices. Other features and benefits are described herein or are apparent from this document, including features and benefits for particular embodiments of the present invention.

Accordingly, the present invention provides a medical device with a tubular body having a proximal end, a distal end, and a longitudinal axis extending at least from the proximal end to the distal end. There may be a plurality of slots formed into the body, and these slots may be configured to enhance the bending flexibility of the body. The medical device may also include a polymer liner inside at least part of the body, which may cover at least some of the slots. At least a portion of the liner may include an anti-collapsing structure.

In various embodiments, the anti-collapsing structure may be in a shape that is helical or annular, or may form a braid. The anti-collapsing structure may be formed from at least one wire, which may be ribbon wire, and may be bonded to the liner. In some embodiments, the anti-collapsing structure may consist of one or more grooves, or at least one corrugation, formed in the liner. In some embodiments, the liner may be formed from at least two polymer layers, and the anti-collapsing structure may be located between these layers. Some embodiments of the present invention have both an anti-collapsing structure and one or more corrugations in the liner, and these corrugations may extend outward or inward from the anti-collapsing structure.

In some exemplary embodiments of the present invention, the slots in the tubular body may substantially define a plurality of segments of the body, and these segments may form a substantially helical pattern at least part way along the axis, and may be arranged so that the segments are separated along the helical pattern by the slots. The segments may be substantially between the end points of adjacent slots, and at least a plurality of the segments may be substantially between the midpoints of two axially adjacent the slots, so that alternating segments along the axis form the substantially helical pattern. In some embodiments, each slot may be substantially in line with at least one other slot, and the segments may be between adjacent substantially in-line slots. Further, in some embodiments, each slot may be substantially parallel to at least two other slots.

In various embodiments, slots may be arranged in a plurality of groups, each slot may be substantially perpendicular to the axis, and each slot in a group may be substantially equally spaced around the axis. Further, each slot in a group may be located at substantially the same location along the axis. As an example, groups may contain two or three slots each, or more. In some embodiments, each longitudinally adjacent group may be rotated around the axis from the previous group forming the helical pattern along the axis described above. The angle that adjacent groups are rotated around the axis may be slightly different than 180 degrees divided by the number of slots in the group. This slight difference may be, for example, more than zero degrees, less than 10 degrees, or both (i.e., within that range). The slots may be arranged with a varying longitudinal spacing (i.e., spacing in the axial direction), and the spacing may generally decrease from the proximal end of the body to the distal end. In some embodiments, the slots may have rounded corners.

In various embodiments, the body of the medical device may be nitinol. Some embodiments may include a central wire disposed at least partially inside the body, which may be slidable inside the body, or may be a core wire, which may be attached to the body. In some embodiments, the central wire may have at least one bend formed therein. In addition, in some embodiments, there may be a hollow annular space between the liner and the body. Further, some embodiments may include a substantially radiopaque marker at the distal end of the medical device. In various embodiments, there may be a coil, which may be oriented coaxially with the tubular body.

The present invention also provides a method of making a medical device with a flexible, kink-resistant tubular member. The method may include the steps of providing a tubular member and providing an anti-collapsing structure concentric with the tubular member. The anti-collapsing structure may have a plurality of sections, and the method may also include the step of deforming the tubular member between the sections into a corrugated shape. In an exemplary embodiment, the anti-collapsing structure may have a helical shape forming a plurality of loops, and the sections between which the corrugations are formed may be the loops of the helix.

In various embodiments, the step of deforming the tubular member may involve applying heat, pressure, or both. Pressure may be applied to the tubular member internally or externally, for example, forming outward or inward corrugations respectively. In some embodiments, tension or compression may be applied to the tubular member in the axial direction, or first tension and then compression. In some embodiments, a mold may be used in the step of deforming the tubular member to form the corrugations. The anti-collapsing structure may be formed from at least one wire, and the wire may be ribbon wire. And the method may further include the step of bonding the anti-collapsing structure to the tubular member.

In some embodiments of the present invention, the bending stiffness of the tubular member or liner may vary along all or part of its length, for example, with a greater flexibility in the distal direction. In various embodiments having a corrugated shape, the variation in bending stiffness may be accomplished by varying the pitch of the anti-collapsing structure, varying the wall thickness of the tubular member, varying the shape of the corrugations, or a combination thereof. In some embodiments, varying the pitch of the anti-collapsing structure may result in variation of the wall thickness of the tubular member, the shape of the corrugations, or both.

In some embodiments, the tubular member may have at least two layers, and the anti-collapsing structure may be located between the two layers. In some embodiments, the method may also include the steps of providing a tubular body, forming a plurality of slots into the body, and arranging the body so that it is concentric with the tubular member.

BRIEF DESCRIPTION OF THE DRAWINGS

FIG. 1 is a side, partially cross-sectional view of one embodiment of a solid medical device configured in accordance with the principles of the present invention;

FIG. 2 is a side partial view of a portion of a medical device showing different types of slots which may be utilized in a solid or tubular guidewire in accordance with principles of the present invention;

FIG. 3 is a side partial view of the tip of a medical device with a radiopaque coil thereabout in accordance with principles of the present invention;

FIG. 4 shows a side partial view of part of an embodiment of a medical device formed with pairs or groups of two slots substantially equally spaced around the axis and substantially perpendicular to the axis, where each slot in each group is located at substantially the same location along the axis in accordance with principles of the present invention;

FIG. 5 shows a side partial view of part of an embodiment of a medical device in accordance with principles of the present invention formed with pairs or groups of two slots substantially equally spaced around the axis and substantially perpendicular to the axis, where each slot in each group is located at a substantially different location along the axis;

FIG. 6 is a side, partial view of a tapered medical device formed with slots in accordance with principles of the present invention;

FIG. 7 is a side, partial view of a solid medical device formed with slots and a coiled tip in accordance with principles of the present invention;

FIG. 9 shows a side view of a core wire of the guidewire of FIG. 8 illustrating the grind profile of the core wire;

FIG. 10 shows a side view of the core wire of the guidewire of FIG. 8 with a medial coil added;

FIG. 11 shows a side view of the core wire of the guidewire of FIG. 8 with a medial coil and a distal marker coil shown;

FIG. 12 shows a side view of the core wire of the guidewire of FIG. 8 with a medial coil, a distal marker coil, and a proximal coil;

FIG. 13 shows a side view of the guidewire of FIG. 8 with a medial coil, a distal marker coil, a proximal coil, and a micromachined tube;

FIG. 16 shows a side view of a portion of a micromachined tube such as shown in FIG. 14 subjected to torsional forces, illustrating deformation or strain from torsional loading;

FIG. 16A shows an isometric view of a slotted tube having three slots per group;

FIG. 16B is a cross-sectional view of the slotted tube of FIG. 16A through a group of slots;

FIG. 16C is a cross-sectional view of the slotted tube of FIG. 16A through another group of slots, illustrating an embodiment of the angle of rotation between adjacent groups of slots;

FIG. 16D is still another cross-sectional view of the slotted tube of FIG. 16A through another group of slots, illustrating the angle of rotation between adjacent groups of slots;

FIG. 26 is a side, partial, cross-sectional view of a metal tubular guide wire or catheter, with a central metal conductor, which device may be suitable for use in making electrical measurements, applying electromagnetic signals to the body, or the like;

DETAILED DESCRIPTION OF EXEMPLARY EMBODIMENTS

Figure 8:
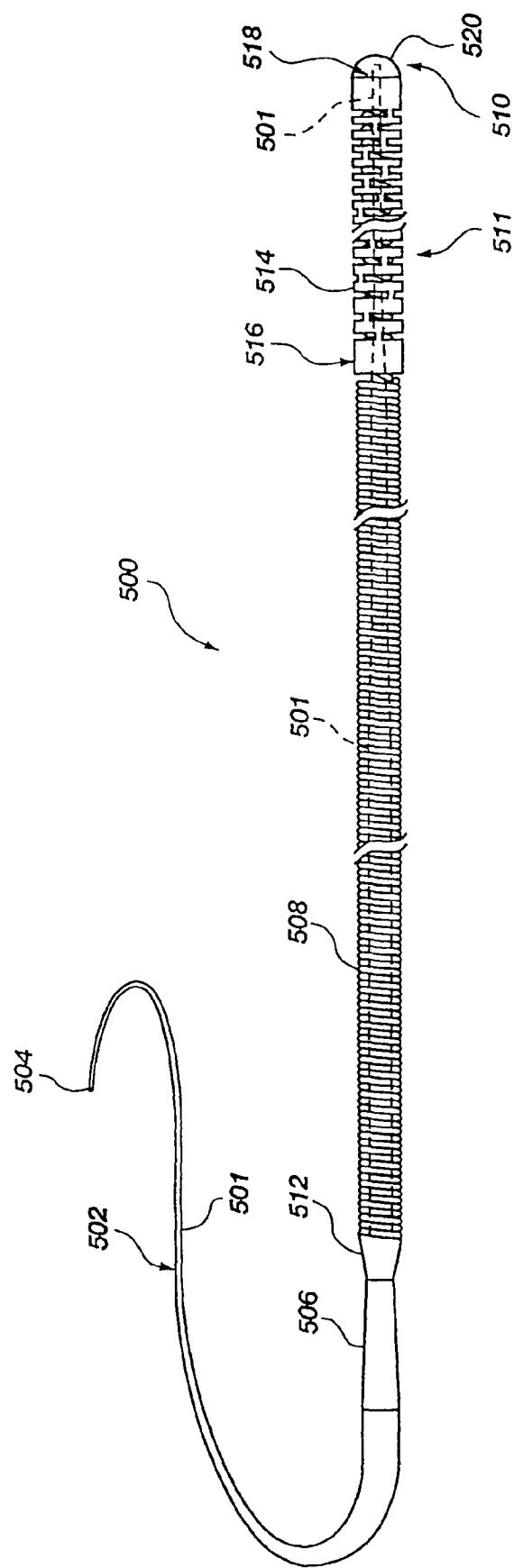
FIG. 8 shows a perspective view of an exemplary guidewire in accordance with principles of the present invention, the guidewire having a slotted tubular body, a solid core, and a coil.

The present invention provides, in an exemplary embodiment, an apparatus such as a medical device, configured to navigate through anatomy. Some embodiments may be used as a guidewire, and may be solid or tubular. Some tubular embodiments of the device may be used as a catheter, or may be used as either a catheter or a guidewire. Some embodiments may navigate like a guidewire, but once in place, perform many or all of the functions that a catheter may perform. Various embodiments are described herein as examples of the present invention, many of which have a body which may be solid or tubular, and is slotted to make it more flexible in bending. Various configurations of the slots maintain, to some degree, the torsional stiffness of the body. In many different embodiments, the body has a proximal end, a distal end, and a longitudinal axis extending at least from the proximal end to the distal end.

One example of a solid medical device is a guidewire, which may be configured to be guided to a target location in anatomy. Referring to FIG. 1 of the drawings, illustrated is one exemplary embodiment of a solid guidewire 200 made in accordance with the present invention. The guidewire 200 includes a proximal end 204, a distal end 208, and a mid-portion 210 disposed there between, with the proximal end being mounted in a pin vise type torquing chuck 212. As would be apparent to a person of ordinary skill in the art, the body of guidewire 200 has an axis extending through it, from proximal end 204, to distal end 208. The body of guidewire 200 may be constructed of nickel titanium alloy, and may range in size from about 0.008 inches to about 0.090 inches in diameter and from about 135 to 300 centimeters in length. In some embodiments, the guidewire 200 may alternatively be made of stainless steel. Four examples of diameter sizes are 0.008 inches, 0.014 inches, 0.016 inches and 0.035 inches.

Slots, cuts, gaps or openings, for example, 216 and 220, may be formed in the guidewire 200 along part or all of the length thereof, which may include the mid-portion 210. These slots 216 or 220, for example, may be formed by saw cutting (e.g., diamond grit embedded semiconductor dicing blade), etching (for example using the etching process described in U.S. Pat. No. 5,106,455), laser cutting, or electron discharge machining. In the examples illustrated, slots 216 are angled to allow for a longer slot and thus greater flexibility, whereas slots 220 are substantially perpendicular to the long dimension or axis of guidewire 200.

As will be discussed in more detail below, in many embodiments the slots may form disks or rings within the body of the guidewire. This configuration may allow the material remaining after the slots are formed to provide bending flexibility in the guidewire, while maintaining relative torsional stiffness. By controlling and varying the spacing, depth and type of slots, the bending flexure profile and torsional stiffness of the guidewire may be selectively modified. Generally, the more closely spaced the slots and the greater their depth, the more flexible the guidewire will be in bending. However, modification of the exact shape, orientation, and spacing of the slots will also allow selective modification or preservation of the torsional characteristics of the cross section somewhat independent of bending flexibility.

The distal end 208 of the guidewire 200 may be preshaped with a bend or curve, as shown, for example to allow for directing the guidewire around curves and bends in vasculature. In other words, the distal end 208 of the device (e.g., guidewire 200) may be curved to facilitate navigation through the anatomy.

To maintain flexibility in the distal end 208, slots may also be provided on that end. Advantageously, the tip may be rounded to minimize the chance of traumatic piercing of body tissue. Also formed on the distal end 208 may be a radiopaque marker or band 224. The band 224 may be, for example, gold or platinum alloy (for X-ray fluoroscopy) or gadolinium or dysprosium, or compounds thereof (for MRI) and may be formed on the distal end 208 by deposition, wrapping or use of shape memory alloy (NiTi) effect to "lock" the band around the end.

In some embodiments, at least some of the slots may have a cross sectional shape that may be, for example, square, rectangular, wedge-shaped, T-shaped, or substantially circular. FIG. 2 is a side, partial view of a guidewire 230, showing three alternative type slots 234, 238 and 240 that may be formed in the body. These type slots provide a kind of built in flexure stop to prevent further flexure of the guidewire when the slot openings close to contact one another and prevent further flexure in that direction. Wedge shaped slots 234 may be formed on opposite sides of the guidewire 230, with the greater width of the wedge being at the bottom of the slot. T-shaped slots 238 may likewise be formed on opposite sides of the guidewire 230, with the cross piece of the T being at the bottom of the slot. Slots 240 may be generally circular as shown. It will be apparent that other slot shapes may also be provided to meet the needs of the user. The slots 234, 238, and 240 are shown oppositely oriented (i.e., on opposite sides of the axis), but it will be apparent that the slots may also be formed at circumferentially-spaced locations about the guidewire, or at alternating locations such as shown and described in more detail with regard to, for example, FIG. 5.

All three types of slots shown in FIG. 2 form segments of material, shown in cross-hatch as areas 232, 236, and 242, respectively, between oppositely disposed slots. As used herein, segments are sections of material remaining between end points of slots or between the end point of a slot and the side of the device. Segments may flex when the medical device bends, and may, for example, be part of a disk (as shown in FIG. 2) or part of a ring (e.g., for tubular embodiments). The configurations of slots and segments illustrated in FIG. 2 may provide at least two distinct benefits. First, it allows the segments to be longer than the gap of the flexure stop. This allows the amount of strain in the segment prior to stop engagement to be controlled by varying the ratio of segment length to gap size, allowing more flexibility, e.g., less bending resistance.

The location and shape of the segment 232, 236, or 242 may also influence the torsional characteristics of the guidewire 230. As is typically well known by those skilled in mechanics, torsional strength is primarily provided by the outer portion of the cross section of a member. Thus, for illustration, a relatively thin-walled pipe will have nearly the same torsional strength as a solid bar of the same diameter because the central portion of the cross section of the solid bar contributes very little to torsional strength. Similarly, by comprising a segment which crosses the entire cross-section of the guidewire 230, in various embodiments of the present invention, the segment 232, 236, or 242 may include a significant amount of the outer portion of the cross section of the guidewire, and therefore transmit varying proportions of the torsional forces from one side to the other of the slots 234, 238, and 240.

For example, segment 232 may be relatively long (measured in the direction of the long axis of the guidewire), but may be relatively deep (measured transverse to the long axis of the segment, and also transverse to the axis of the guidewire) and will therefore transmit a relatively large amount of torsional force. Segment 236 may be longer and thinner than segment 232, and may therefore transmit a smaller amount of torsional force across the slot 238. Of the examples given in FIG. 2, segment 240 may be the shortest and strongest of all, and may transmit the greatest amount of torsional force. However, given the size and shape of slots 240, this configuration may provide the greatest flexibility. Because the small flexure stop gaps of slots 234, 238, and 240 may be varied in width without changing the depth or overall shape of the slot, the flexibility of the guidewire section may be selectively altered without affecting the size or strength of the segment. Thus, the bending flexibility and torsional strength of the guidewire may be selectively and relatively independently altered.

In some embodiments of the present invention, longitudinally adjacent pairs of slots may be rotated about 90 degrees around the wire from one another to provide bending flexure in both directions. However, the slots may be located to provide preferential flexure in only one, two, three, etc. directions, in applications where such properties are desired. In some embodiments, the slots may be randomly formed which may allow bending (flex) equally, non-preferentially in all directions or planes.

FIG. 3 shows an exemplary embodiment for applying a radiopaque marker to the distal end of the body of a guidewire 244, shown in side, partial, cross-sectional view. An annular trough, groove, or channel 248 may be formed at the tip of the guidewire 244, and a radiopaque wire coil 252, which may be made of platinum alloy, may be wound about guidewire 244 in channel 248. The coil 252 may be welded or soldered to itself or to guidewire 244 to hold coil 252 in place at the tip of guidewire 244. In some embodiments of the present invention, a gold or platinum band may be used rather than a coil, for example, on a nickel titanium alloy guidewire. In such embodiments, the guidewire may be cooled and shrunk to allow the band to be placed on the wire. Then when the guidewire returns to room temperature, the band may be maintained in place on the guidewire, for example, via an interference fit, without the need for welding or soldering or other joining mechanism.

FIG. 4 is a side, partial view of the body of a solid guidewire 260 formed with opposing slots 264 spaced along a portion of the guidewire, and opposed slots 266 rotated 90 degrees from opposed slots 268. As with slots 266, the rotated slots 268 may be arranged in opposing pairs, with opposite slot corresponding to 268 not visible on the far side of the guidewire. The slots may be formed to provide preferential bending (flex) in one plane, or may be positioned to allow bending in multiple planes. This may be achieved, in some embodiments, for example, by rotating adjacent pairs of slots by 45 degrees with respect to one another or some other selected angular amount. Also shaded in FIG. 4 are the ring sections 262 between adjacent opposing slots 264. It will be apparent that the pairs of rotated slots 268 will also form segments there between, except that these segments will be oriented at an angle of 90 degrees relative to the segments between slots 266.

FIG. 5 is a side, partial view of the body of a solid guidewire 270 formed with staggered or offset slots 274 on opposite sides of the guidewire. A curved distal end 278 is also shown with a radiopaque marker band 280. As with the FIG. 4 embodiment, certain pairs of offset slots may be rotated with respect to the other pairs, to thereby control direction of flexure. This configuration also presents particular advantages regarding torsional control. As may be evident from FIG. 4, opposed slots produce thin flexure segments 262 between the bottoms of each pair of opposed slots. The dimensions and flexure properties of these segments may be determined by the depth, separation and width of the slots and so the flexibility of a guidewire with opposed slots may be controlled by varying these parameters.

Offset slots, as indicated in FIG. 5, produce disks 272 in the area between each pair of adjacent slots, at least a portion of which may allow flexure. Depending on the depth of the slots 274, segments 276 between the base of each slot and the opposing side of the guidewire may also allow flexure.

It will be apparent that the flexure properties of this guidewire may be determined not only by the depth and width of the slots (as with opposed slots) but also by the offset (axial spacing) of the slots. Consequently, the flexibility of a guidewire with offset slots can be controlled by varying some or all of these parameters. Also, the flexibility may be varied simply by controlling the degree of the offset while keeping the depth and width of the slots constant.

Offset slots provide advantages in some applications because it may be more practical to produce a consistent pattern of this type of slot than with opposed slots. Very flexible sections with opposed slots require very deep and/or wide slots, and controlling either parameter may involve a high degree of precision in some embodiments since very deep slots may overly weaken the guidewire and very wide slots may result in catching on and/or damaging tissue through which the guidewire may be threaded. Very flexible segments using the offset slot pattern, on the other hand, may be produced without the need for either deep or wide slots, but rather by simply varying the distance or separation of the offset slots, and it may be less difficult to obtain the required accuracy.

FIG. 6 is a partial view of a solid guidewire having an enlarged proximal section 288, which may provide a relatively high torsional stiffness, and a narrowed distal section 292, covered by a hydrophilic polymer sleeve 294. For example, the enlarged section 288 may be 0.014 inches in diameter and the narrowed section 292 may be 0.010 inches in diameter. The distal end 296 of the guidewire may be formed with slots as shown and described herein. In some embodiments, slots may also be provided at other locations of the body, in the narrowed section 292 or in the enlarged section 288, to increase bending flexibility while maintaining high torsional stiffness.

FIG. 7 is a side partial view of a solid guidewire 300 having a tapered distal end 304 about which is coil 308, which may be made, for example, of platinum alloy. Disposed at the tip of the distal end 304 of the guidewire, and at the end of the coil 308, may be a solder ball 312. Slots 316 may also be formed in the body of guidewire 300 as shown and described herein. In addition to the use of slots to control the flexure of a guidewire, nickel titanium alloy guidewires can be heat treated to vary the flexure characteristics. For example, selective annealing along the length of the wire can change the stress/strain relationship of the material, and thus the flexure properties.

In the embodiments of the present invention described herein, the medical device can be made "flow directable" by providing highly flexible distal ends. "Flow directability" means that the distal end of the device tends to "flow" with the fluid, for example, blood, around curves and bends in a vasculature passageway.

To reduce resistance to movement of a medical device in a vasculature passageway, the surface of the device may be electropolished to increase the smoothness thereof, a lubricious coating may be applied to the surface, or both. Such coatings might include, for example, silicone based oil, polymers, hydrophilic polymers, or some combination of these. In some embodiments, a lubricious sleeve made of a hydrophilic polymer, for example, may be provided for disposal over the medical device.

With reference to FIG. 8, guidewire 500 is an exemplary embodiment in accordance with principles of the present invention, which may be configured to be guided to a target location in anatomy. Guidewire 500 comprises a proximal portion 502 extending from a proximal end 504 to a first transition portion 506 where the diameter of guidewire 500 may change. Guidewire 500 has a longitudinal axis extending from proximal end 504 to distal end 510. The axis may be common for various components, for example, core wire 501, coil 508, and slotted tube or body 514, and the axis may extend beyond such individual components.

It should be noted that FIG. 8 is illustrated in perspective view, and proximal end 504 may have a diameter that is greater than or equal to the remainder of guidewire 500. Proximal portion 502 may comprise a stainless steel core wire 501 which may be solid wire and may have a circular cross section. Core wire 501 of proximal portion 502 may be covered with a low friction coating. For example, polytetrafluoroethylene (PTFE) may be used to coat proximal portion 502. The proximal portion may have a diameter as large as needed to transmit torque sufficient for the intended use of guidewire 500. For coronary and some peripheral uses for example, a diameter of about 14 thousandths of an inch may be appropriate.

At the first transition portion 506, the stainless steel wire may be ground to a smaller diameter, transitioning over an axial length sufficient to provide a smooth transition. This may be about 2 inches long in one embodiment. Beginning at and distal of the first transition portion 506, guidewire 500 may have a more complex configuration. Specifically, a proximal coil 508 may be disposed over the stainless core wire 501. The core wire 501 may continue to the distal end 510 of guidewire 500, and the proximal coil 508 may enclose or overlay core wire 501 as will be further explained. The proximal coil 508 may be attached to core wire 501 at first transition portion 506 by a proximal solder joint 512, which may be at a point where the inner diameter of the coil matches the outer diameter of the core wire. The diameter of the core wire 501 may continue to decrease in the distal direction under the proximal coil 508, and beyond in some embodiments.

In many embodiments of the present invention, at the distal end of the proximal coil 508 of guidewire 500 comprises a slotted tube 514, which may be formed of a superelastic material such as NiTi alloy. Tube 514 may be referred to herein as the body of guidewire 500, and as shown, has a proximal end, a distal end, and a longitudinal axis extending at least from the proximal end to the distal end. The axis of body or tube 514 may be common with the axis of guidewire 500, thus extending beyond tube 514. The slots may be formed, for example, by micromachining. This slotted tube 514 may effectively transmit torque to the distal end 510 of the guidewire, but may be very flexible in bending. The slotted tube 514 may enclose or overlay additional structure as will be described below. The slotted tube 514 may be attached to the proximal coil 508 via other underlying structure, and the core wire 501 at a medial joint 516. Medial joint 516 may comprise, for example, solder, glue, or both. The location of this joint 516 may be the point where the torsional stiffness or torsional strength of the core wire 501 is substantially equal to that of the slotted tube 514. Thus, the torque may be transmitted through the core wire from proximal end 504 of guidewire 500 to the medial solder and glue joint 516, then substantially through slotted tube 514 to distal end 510 of guidewire 500.

The view of FIG. 8 is generally not to scale, and various components may be longer that what is shown relative to their diameter. The outer diameter of the proximal coil 508 may be substantially the same as the diameter of proximal portion 502 of core wire 501. The outer diameter of the slotted tube 514 at the distal tip portion 511 of guidewire 500 may also be approximately the same. For example, all of these diameters may be about 14 thousandths of an inch. In one embodiment the proximal coil 508 is about 11 inches long and the distal tip portion 511, including the slotted tube 514, is about 2 inches long. Although not shown, the distal tip portion 511 may have a curved or bent configuration.

At distal end 510 of guidewire 500, slotted tube 514, underlying structure (not shown), and core wire 501 may be attached at a distal joint 518. Distal joint 518 may, for example, comprise solder, glue, or both. The distal joint 518 may comprise an adhesive 520, which may be formed into a rounded configuration at the distal end 510 of the guidewire 500 to form an atraumatic tip. The core wire 501 may have a very small diameter at the distal end 510. For example, the grind profile may reduce the diameter of core wire 501 to approximately 2 thousandths of an inch at or near distal end 510.

Turning to FIGS. 9-13, the construction of an exemplary guidewire configuration will be described in more detail. With reference particularly to FIG. 9, the core wire 501 alone may be seen to advantage, with the grind profile appreciable. Core wire 501 may have a rounded configuration at the proximal end 504 of the wire, and the proximal portion 502 may be as previously described, and may be about 65 inches in length in one exemplary embodiment. The grind profile may extend about 14 inches further to the distal end 510 of the guidewire 500. In addition to the first transition portion 506, a second 522 and a third 524 transition portion may be provided. Distal to the first transition 506, which as mentioned may be about 2 inches in length in the exemplary illustrated embodiment, the core wire 501 may have a first reduced diameter portion 526 which may have, for example, a length of about 6 inches and a diameter of about seven and a half thousandths of an inch. The second transition portion 522 may also be about 2 inches in length, and the diameter may further reduce from that of the first reduced diameter portion 526, for example, to about five and a half thousandths of an inch. This diameter may be maintained, for instance, for about two and a half inches, to form a second reduced diameter portion 528. The diameter may further decrease at third transition portion 524, for example, to about two thousands of an inch, which may be maintained to the distal end 510, to form a third reduced diameter portion 530. This third transition portion 524 may be, for example, about one tenth of an inch in length, and the third reduced diameter portion 530 may be about one and nine tenths inches in length in the illustrated exemplary embodiment. The third reduced diameter portion 530 may be configured to be extremely flexible in bending, but may retain sufficient axial strength to help prevent distal tip separation on withdrawal of the guidewire from a position where the tip is stuck in the anatomy. It may be necessary that sufficient stiffness is present to facilitate pushing the distal tip portion 511 of the guidewire 500 during insertion.

With reference to FIG. 10, the underlying structure mentioned before of some exemplary embodiments will now be described. A medial coil 532 may be attached to the core wire 501, for example, at the third transition portion 524. The medial coil may, for example, have an outer diameter substantially equal to the inner diameter of the proximal coil 508, or substantially equal to the inner diameter of the slotted tube 514. Medial coil 532 may be attached by soldering, and this location of attachment on the third transition portion 524 may also be the location of the medial joint 516 mentioned above. Also, it will be noted that the location may be near the proximal end of the third transition portion 524, so that the diameter of the core wire 501 at this location may be substantially the same as the second reduced diameter portion 528. As the core wire 501 transfers torque to the slotted tube 514 at this location as mentioned above, the location on the grind profile may be important as it may be substantially the end of the line for torque transmission through the core wire 501. The diameter of the core wire 501 may determine the amount of torsional force that can be transmitted and the torsional stiffness, and the location of joint 516 and diameter of core wire 501 at that location may be chosen in conjunction with selection of the parameters of the slotted tube 514, so that the torsional strength or stiffness is substantially equal in core wire 501 at or proximal to joint 516, and in slotted tube 514.

The medial coil 532 may be formed of stainless steel, and the individual coils of medial coil 532 may be closely spaced or touching, at least over part of the length of medial coil 532. In some embodiments, medial coil 532 may have a proximal portion 534 at its proximal end, where the individual coils are not as closely spaced in the axial direction, and are not touching each other. This may aid in more secure bonding to the core wire 501, at least in part because the greater coil spacing may facilitate a slight deformation in the coils allowing them to follow the grind profile more closely. The medial coil may also have a distal portion 536 where the individual coils are not as closely spaced in the axial direction, and are not touching each other, which will be further described next.

Turning to FIG. 11, a distal coil 538 may be disposed, for example, over the third reduced diameter portion 530 at the distal tip portion 511. The proximal end of distal coil 538 may be provided with a portion 540 where the individual coils are not closely spaced in the axial direction. The proximal end of distal coil 538 may fit together with the distal portion 536 of the medial coil 532 to form a secure interlock by intertwining of the coils and then soldering. The distal coil may be of slightly larger diameter wire, due to the reduced grind profile it overlays, but the outside diameter may be slightly less than that of the inside diameter of the slotted tube 514 (not shown). The distal coil 538 may be formed of a radiopaque material in the illustrated embodiment to provide enhanced fluoroscopic visibility. Platinum, gold, palladium, or dysprosium may be used for this purpose. An increased diameter wire may further provide more radiopacity. The distal coil thus may act as a marker to aid in navigation of the guidewire within the anatomy of a patient.

The drawing figures are not to scale, and the distal coil may be considerably longer than the medial coil 532. In some embodiments, the distal end of the distal coil may be soldered to the core wire 501 adjacent the distal end 510 at the location of the distal solder and glue joint 518.

With reference to FIGS. 9-12, the guidewire 500 apparatus may be assembled by attaching the medial spring 532 to the core wire, then attaching the distal (marker) coil 538 to the medial coil, then the proximal coil 508 may be slipped over the assembly and soldered to the core wire 501 at the proximal solder joint 512 and to the medial coil 532 at the location of the medial solder and glue joint 516. The solder used throughout may be a silver or gold alloy solder or another material regulatory-approved for such use.

With reference to FIG. 13, fabrication of the guidewire 500 may be completed by placement of the body or slotted tube 514 over the distal tip portion 511. Slotted tube 514 may be fixed in place by securing it at its proximal end at the medial solder and glue joint 516 with an adhesive. This adhesive may be a UV cured regulatory-approved adhesive such as Dymax. Slotted tube 514 may also be attached at its distal end to the distal tip of the core wire 501. Slotted tube 514 may also be attached to the distal (marker) coil, for example, by an identical or similar adhesive. As mentioned, this adhesive may form a rounded tip 520 to reduce trauma, and may also form the distal solder and glue joint which holds together the core wire, distal marker coil, and the slotted tube 514 at the distal end 510 of the guidewire.

In comparing 0.014 inch diameter micromachined NiTi tubing as disclosed herein to conventional guidewire configurations and stainless steel tubing, the micromachined tubing may be superior to conventional guidewire configurations when the diameter of the stainless steel core wire drops below about 5 thousandths of an inch on the grind profile. Little or no advantage may be obtained when the core wire is this diameter and larger. Thus, there may be no reason to provide micromachined tubing proximal of the point where the grind profile drops to this size. Accordingly, the medial solder/glue joint (516 in the figures.) may be located substantially at the point where the core thins to about 0.005 inch diameter. As explained, the NiTi tubing or body which has been micromachined as described herein provides a superior path for transmission of torque to the distal tip 510 of the guidewire from that point while at the same time facilitating bending. Thus, the exemplary embodiment illustrates that the guidewire configuration can be optimized for cost, the less expensive stainless steel core wire and conventional coil configuration being provided up to the point where better characteristics are obtainable with a micromachined configuration.

The guidewire may further include a micromachined barcode identification 142 located, for example, adjacent the proximal or distal end of the guidewire. The barcode may be made by very lightly scoring the surface to form a binary code to encode identifying information regarding the catheter. This may be done by a similar process to that used to micromachine the tubing 514.

Other features of the guidewire can include providing lubricious coatings on components distal of the proximal portion 502 previously described as including such a coating. For example a silicone coating as may be applied in one of the many manners known in the art.

Another feature may be that the slotted tube 514 may be deburred after micromachining. For example, an acid wash etching process can be used to deburr the inner surfaces, and the tubing can be placed on a mandrel and turned while being subjected to an abrasive jet to deburr and round the micromachined edges to minimize the possibility of catching on anatomy.

Figure 14:
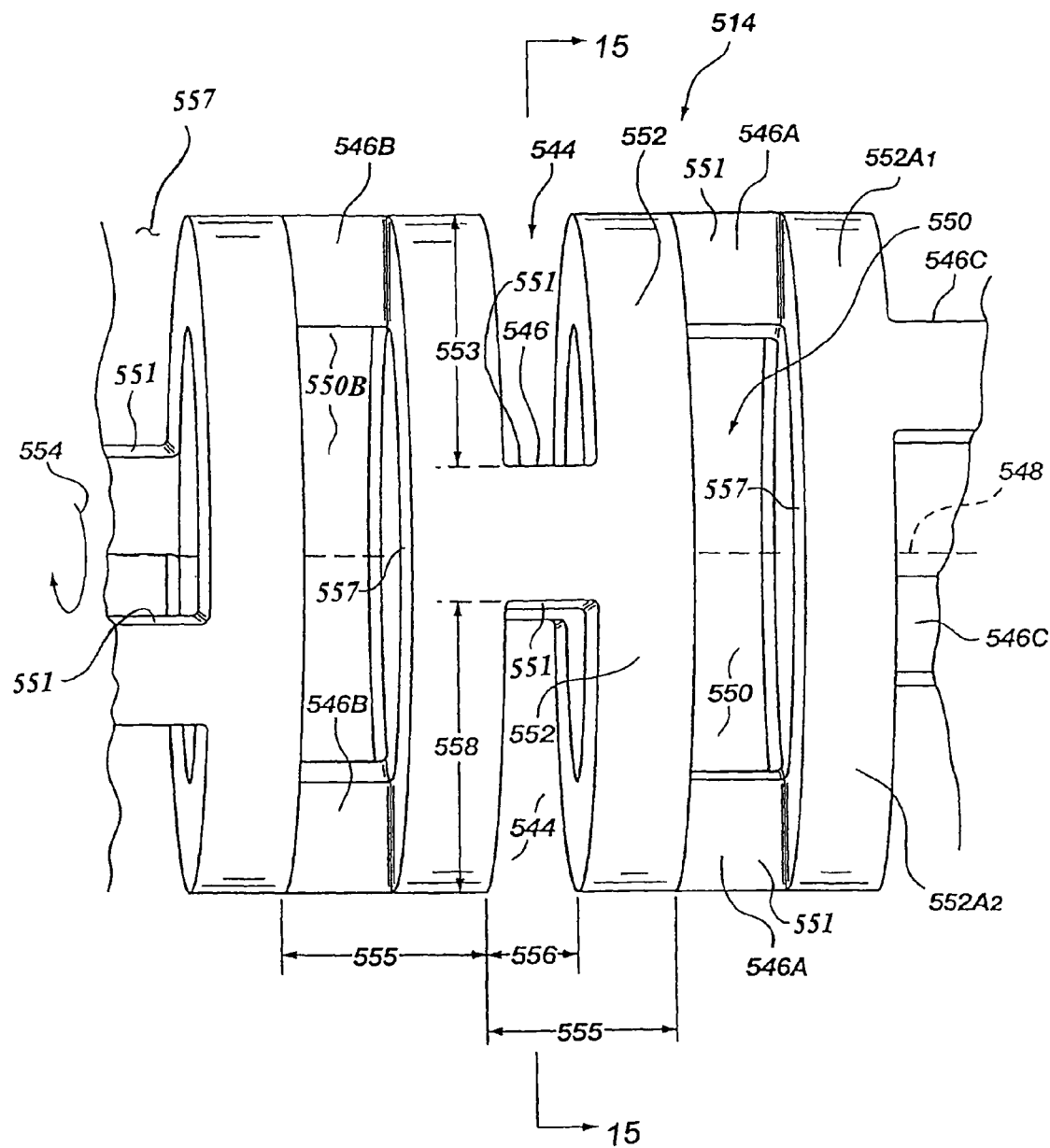
FIG. 14 shows a side view of a portion of a micromachined tube in accordance with principles of the invention, illustrating an exemplary embodiment of the geometry of the micromachined tube or body.

Turning now to FIG. 14, a section of a slotted body or tube 514 is shown to illustrate in more detail an exemplary embodiment of the structure. In the embodiment shown, axis 548 is the longitudinal axis of body 514, and may extend beyond body 514, for example, through core wire 501 shown in FIG. 8. In the exemplary embodiment illustrated in FIG. 14, the device has slots, for example, 544 and 550, that are arranged into a plurality of groups of slots formed into the body, and each slot illustrated is substantially perpendicular to the axis 548. In the embodiment shown, for at least the plurality of pairs of slots shown, the slots in each group are at substantially the same axial location. Also as shown, each slot is substantially perpendicular to axis 548, and each slot is substantially equally spaced around axis 548. Thus, each of the segments in a group is substantially the same size, for example, segments 546 between slots 544. In the embodiment illustrated, each group of slots contains two slots, i.e., a pair of slots. Also as shown, each slot 544 in each group is on substantially opposite sides of the axis 548. FIGS. 16A-16D illustrates another exemplary embodiment of body or tube 514 wherein each group of slots contains three slots 550.

Although not shown in FIG. 14, the slots, for example, 544 and 550, may have radiused or rounded inside or outside corners, or both. Rounded outside corners may reduce trauma to anatomy or vasculature as body 514 is rotated, advanced, or withdrawn. Rounded outside corners may also reduce friction between body 514 and the anatomy or between body 514 and an external sleeve or catheter. Outside corners may be rounded, for example, by polishing body 514 after cuts 544 or 550 are formed. For instance, body 514 may be abrasive blasted or bead blasted after cuts 544 and 550 are formed. Rounded inside corners, for example as illustrated in FIGS. 4, 5, 18, 21, 22, and 23, may reduce stress concentration, and may be formed, for example, by rounded outside corners on the blade used to cut the slots, for example, slots 544 and 550.

Figure 15:
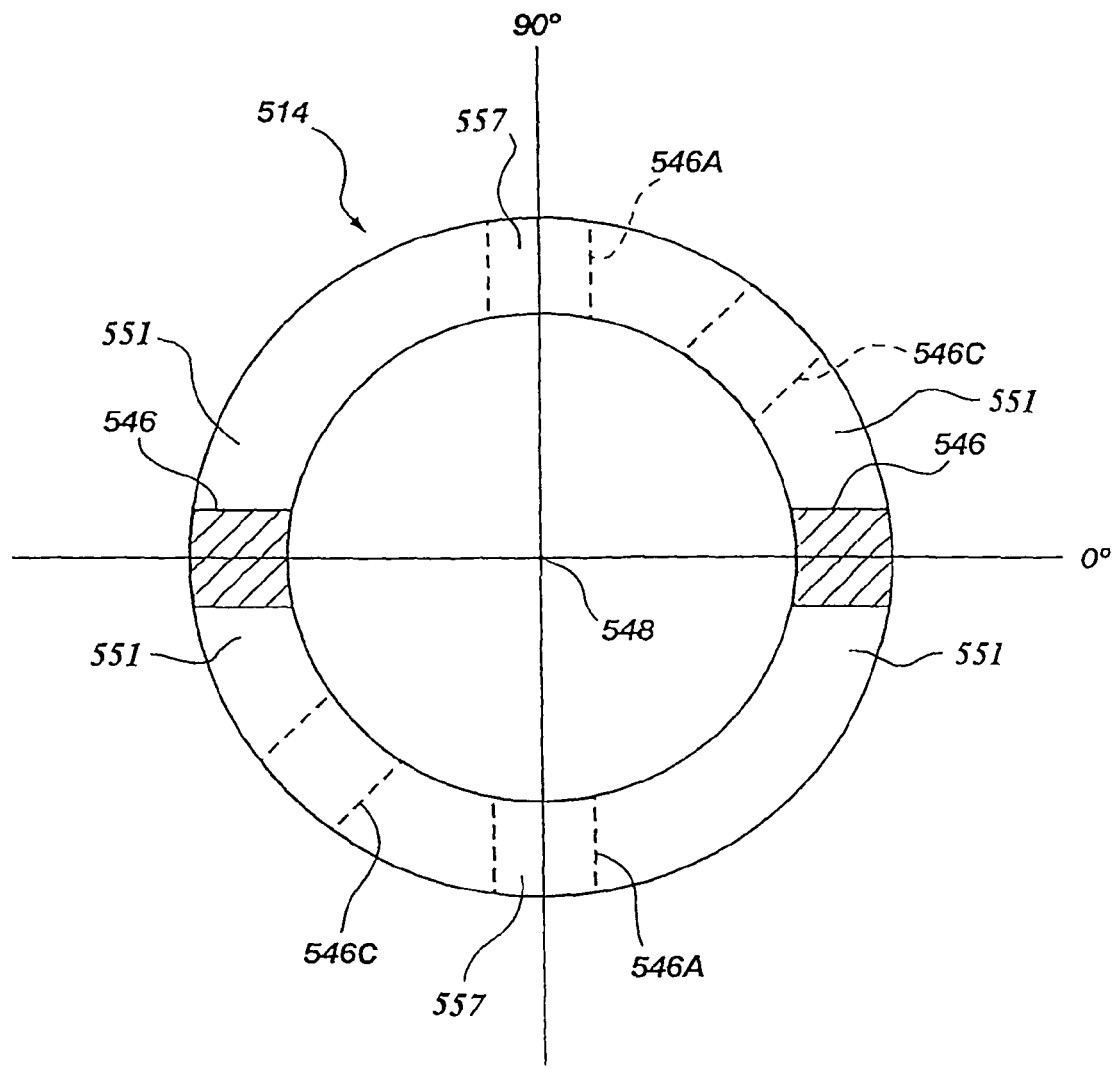
FIG. 15 shows a cross-sectional view, taken along line 15-15 in FIG. 14, of the slotted tube or body shown in FIG. 14.

In some embodiments, the slots may be opposed cuts. For instance, as illustrated in FIG. 14, two cuts 544 may be made from opposite sides of the tubing or body 514 at the same location along the longitudinal axis of the body 514. As shown in FIGS. 14 and 15, slots may have two end points and a midpoint, for example, end points 551 and midpoint 557.

In addition, in the embodiment shown, each slot is substantially in line with another slot. For example, slot 544 at the top of FIG. 14 is in line with slot 544 at the bottom of FIG. 14. As used herein, two slots are substantially in line if the two slots are in substantially the same line, for example, a line through the surface of body 514. In the embodiment shown, segment 546 is between adjacent and substantially in-line slots 544. Specifically, segment 546 is between ends 551 of slots 544.

In many embodiments, slots are parallel or substantially parallel, for example, to other slots. As used herein, slots that form parallel planes are considered to be parallel. For example, slots 544 are parallel to each other, and are parallel to slot 550. Slots that form lines in the surface of body 514 are also parallel if the lines in the surface of body 514 are parallel.

As shown, for example, in FIG. 8, there may also be a varying longitudinal spacing between adjacent groups of slots, which may decrease from the proximal end to the distal end, for example, to vary the bending stiffness of the device along the length of the body.

Focusing now on the material that is left in body 514 after the slots, for example, 544 and 550 are formed, FIG. 14 shows a tube or tubular body 514 slotted to form rings 552 and segments 546, where segments 546 have the shape of part of a ring. However, other embodiments may be formed from a solid cylinder, for example, and may be slotted to form disks and segments that have the shape of part of a disk. Segments, for example, 546A, may connect rings, for example 552 and 552A. Thus, the slots may substantially define a plurality of segments of the body that may connect shapes that are also defined by the slots. These shapes may be, for example, rings or disks. FIGS. 16A-16D illustrate an embodiment of tube or body 514 having three slots 550 per group forming rings 552 and segments 546.

The segments may be substantially between end points of adjacent slots. For example, slot 546 is between end points 551 of slots 544. Segments may also be substantially between midpoints of axially adjacent slots. For example, as illustrated in FIG. 14, segment 546 is substantially between midpoints 557 of slots 550 and 550B. The depth of the slots may be controlled to leave a segment 546 of the tubing wall extant between the slots, for example, on each of the opposite sides (180 degrees apart) of the tubing.

These segments 546 may act to carry forces across the slot area at that location along the longitudinal axis 548 of the tubing. These segments may carry or transfer forces from adjacent structure (e.g., rings) on one side to adjacent structure on an opposite side. In other words, the segments may connect the rings, or other shapes. For example, segments 546A connect rings 552 and 552A.

When a group of opposed slots 550 is made adjacent to the slots previously described (544) the location of the slots may be made such that the segments 546A formed by the second set of slots are displaced circumferentially from the adjacent segments 546. This may be done by rotation of the tube or body 514 relative to the saw used to slot the tubing through some angle before cutting the slots. This can be seen in FIG. 15. Thus, as illustrated in FIG. 14, the segments, for example, 546 and 546C, may form a substantially helical pattern at least part way along axis 548, and these segments may be separated along this substantially helical pattern by slots, for example, slot 550. As illustrated, the helical pattern is formed by alternating segments along the axis 548. For example, the helical pattern is formed by segments 546 and 546C, but segments 546A are not part of this helical pattern, although segments 546A may be part of another helical pattern, for example, with segments 546B. Each of these helical patterns may be formed by alternating segments along the axis, for example, segments formed by every other group of slots along the axis.

Some or each longitudinally adjacent (adjacent along axis 548) group of slots may be rotated around axis 548 from the previous group to form the helical pattern. The amount of rotation between axially adjacent groups of slots, for example, forming the helical pattern described, may be selected with each successive slot to give a pattern calculated to facilitate torque transmission while also facilitating bending of the tube after machining. Various exemplary embodiments of this slot distribution are discussed herein, for example, with reference to FIGS. 18 and 19 below.

With reference further to FIG. 14, in addition to segments, rings 552 or other shapes may be created. In the exemplary embodiment illustrated in FIG. 14, rings 552 are shown. The rings 552 are the curved annular portion of the tubing wall between adjacent slots, for example, 544 and 550, and between adjacent segments, e.g., 546 and 546A. These rings may carry forces from a particular set of segments to the two adjacent segments created by the adjacent set of slots.

With reference to FIG. 16, once a tube 514 has been fabricated and a torquing force is applied, the machined tube will tend to deform the segments and rings, e.g., 546 and 552. In order to optimize the machined tube for maximum torque transmission, the goal may be to match, insofar as possible, the strain in the segments and rings all along the length of the wire. This may be, for example, so that one or the other will not constitute a weak point which will fail by deformation well before that of the adjacent segments or rings when the torquing force is applied. With reference to FIG. 14, this matching can be done in tubing of constant cross section by variation of several parameters, namely the location (spacing 555 between), width 556, and depth 558 of slots (e.g., 544, 550) made. Wider spacing of slots creates wider rings, and shallower slots create wider segments. Likewise, more closely spaced slots create narrower rings, and deeper slots create more narrow segments. Wider slots create longer segments. The configuration of the slotted tube 514 may be defined by calculation, using well-known formulas for stress and strain. The design process can further include finite-element analysis of the configuration to give localized stress and strain values. The calculations may be repeated as necessary using incrementally changing parameters to optimize the design taking into account the concepts set forth herein.

When a slotted tube or body 514 is bent along its axis, flexure may occur in segments 546, rings 552, or both. Embodiments having two slots 550 per group (e.g., as shown in FIG. 14) may have more flexure in the segments 546, as compared with embodiments having three (e.g., FIG. 16A) or more slots per group. Thus, fatigue in segments 546 may be reduced by having three or more slots 550 per group. In some embodiments, having three or more slots 550 per group may reduce the maximum strain in comparison with embodiments of the same bending stiffness with two slots 550 per group.

As a practical matter in manufacturing, a saw blade of a specified width may be used. And accordingly, the width of all slots may be held to this value. In the illustrated embodiment, a diamond silicon wafer cutting saw blade (as may be used in the microprocessor and memory chip manufacturing art) about one thousandth of an inch wide may be used to make the cuts or slots (e.g., 544). While it may be possible to make wider slots by making a first slot, then moving the wire relative to the blade by a distance up to a width of the blade, and repeating as necessary for wider slots, speed of fabrication may be higher if a single slot is used. Therefore, using this constant slot width, the possible variables may be depth 558 of slot and spacing 555.

Given that slot width 556 may be desired to be held constant, in one embodiment the other parameters may be selected as follows. The bending stiffness desired at any selected location along a length of tubing may be obtained by selection of an appropriate spacing 555 between slots. Given that the width of each slot may be the same, in the calculations, selection of a distance between the set of opposed slots to be made (e.g., 546A) and the last set of opposed slots made (e.g., 546) will define, by means of the calculations, the depth of the slots to be made as the distance between slots defines the width of the rings, and the width of the rings may be related to the width of the segment by the condition of equality of strain values to be obtained for a given applied torsional force 554.

The locations of the segments 546 may be determined by the relative angular displacement of the adjacent sets of opposed slots. The width of the segments depends on the depth of slots. The length of each segment may be the same and equal to the constant slot width (e.g., one thousandth of an inch). The depth of each slot may be determined by comparison of the strain in each of the resulting segments (they may be assumed to be the same, though in fact they may not be in all cases due to differing force distribution due to variations in geometry) and then matching the strain in the segment(s) (e.g., 546) with the strain in the shapes or ring(s) (e.g., 552). Four sections of ring may be created between each set of opposed slots. The resulting strains may be evaluated in each of the four sections, but in one embodiment another simplifying assumption may be made that the strain in the two shorter sections is the same, and likewise the strain in the two longer sections of ring is the same. The greater of the resulting maximum strains in the rings may be compared with the maximum strain in the segments. The depth of slot 558 may be varied until the strains are matched. This value may be then used in making the slots at that location.

Other factors may be taken into consideration. For example, there may be a practical limit on the size of segments and rings. Too large at the desired advantages may be lost, too small and imperfections in materials and variations within the tolerances in machining may compromise performance. This may be influenced by the thickness of the tubing, the size of the saw blade, accuracy of the machining apparatus, etc. Generally speaking, segments or rings having dimensions on a par with or smaller than the width of the cutting blade used to micromachine them should be avoided in many applications.

In one embodiment, the design process may include spacing the slots (e.g., 544, 550) apart along the axis 548 of the tubing so as to provide bending as desired. The slots may be closer together to give less resistance to bending, and more spaced apart to give more resistance to bending. (See, for example FIGS. 8 and 13, where the tube 514 becomes more flexible toward the distal end 510 of the guidewire 500.) The stiffness can be controlled by varying the spacing 555 of the slots, the other parameters being selected as appropriate as described above. The bending stiffness of the tubing can vary along the longitudinal axis, for example being made to gradually become less stiff toward the distal end, by gradually decreasing the spacing between slots as in the above example.

As discussed, the depth 558 of the slots may be calculated using stress/strain relationships to match the strain in the segments 546 and rings 552 created. In one embodiment, the greatest strain in the segments may be matched to that of the greatest strain calculated in the rings. Alternatively, another method may be employed, for example comparing the strain in a given segment 546A to that of the rings 552, 552A on either side of the segment along the axis 548 of the tubing 514 to match the strain. In another embodiment the average of the highest strain values in rings 552, 552A1, 552A2 (552A1 and 552A2 being of unequal length the strains may be markedly different), on either side can be used to match the strain in the segment 546A under consideration. Varying the thickness of the segment(s) affects the forces transmitted to the rings and therefore varies the stress and strain in the ring; so, as a result, many iterations of these calculation steps may be required to optimize the design. Likewise, adjustment of the size of one set of segments and rings will affect the stresses and strains in adjacent sets of segments and rings, so additional calculations and re-calculations may be required to optimize by matching strain throughout all the adjacent segments and rings. Practical considerations may require the use of a computer and appropriate algorithm programmed therein to optimize these design parameters.

With reference again to FIG. 15, the distribution of the orientation of adjacent slot groups giving rise to the segments 546 left after the slots are made, will now be discussed. The object may be to provide a distribution of slot orientations along the length of the tubing that minimizes preferred bending directions of the slotted tube 514 giving rise to undesirable effects collectively referred to as whip or a deviation of expected rotational result at the distal tip of the guidewire from that expected by the user from rotational inputs made at the proximal end of the guidewire by turning chuck 212 shown in FIG. 1.

Figure 17:
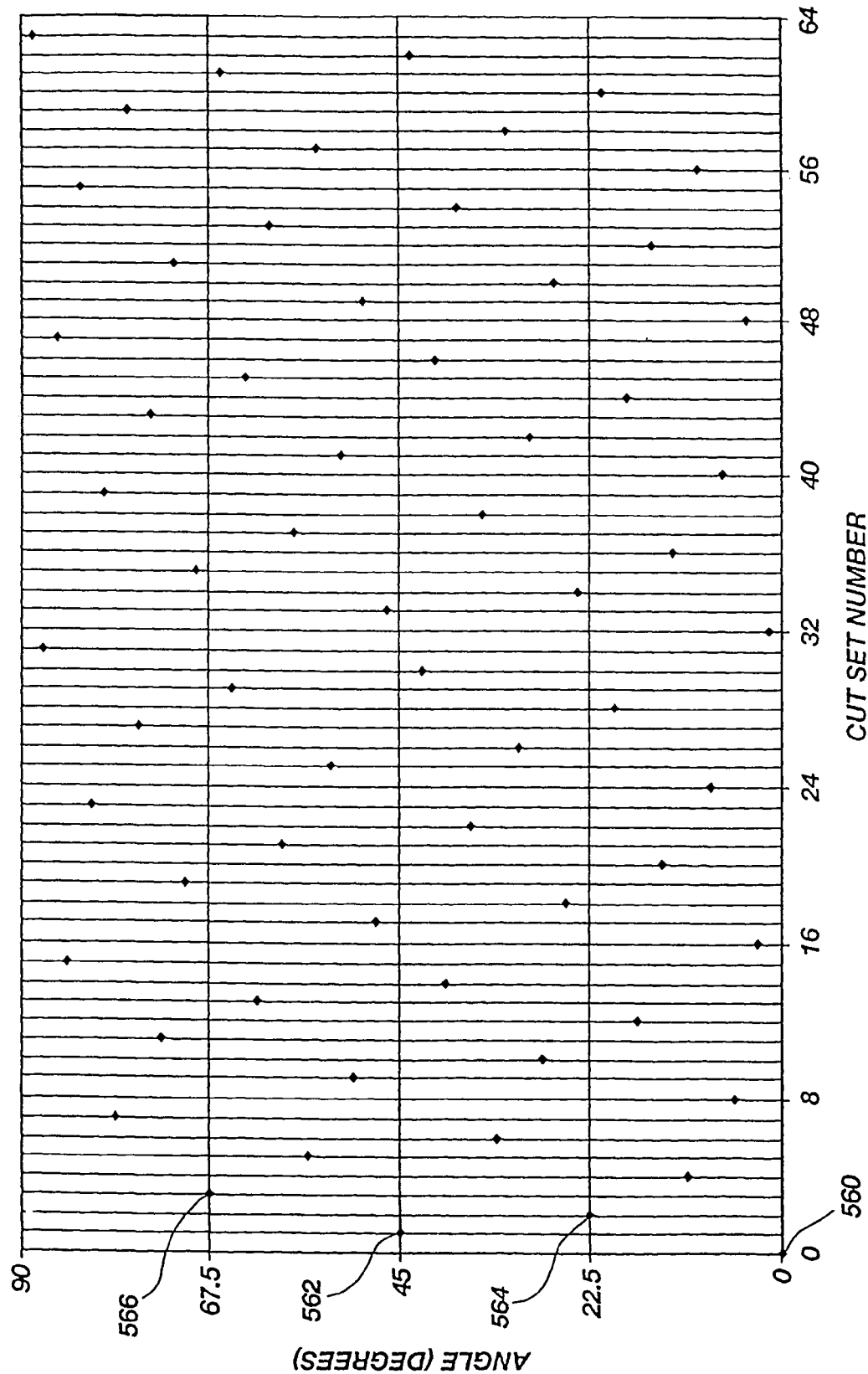
FIG. 17 shows an example of a slot orientation distribution progressing in an axial direction along a micromachined guidewire segment.

With reference to FIG. 17, in embodiments having two slots per group, one way of organizing the slot distribution to minimize whip is to assume a first pair of opposed slots (180 degrees apart) and a second pair of opposed slots immediately adjacent will be offset by an angle of ninety degrees. Collectively the four slots will be referred to as a first slot set 560. A second slot set 562 of adjacent opposed slots oriented ninety degrees apart may be subsequently made, these being oriented with respect to the first slot set (designated arbitrarily as oriented at 0 degrees) so as to be rotated 45 degrees. The next similar slot set 564 may be oriented at 22.5 degrees, and the next at 67.5 degrees, and so on in accordance with the distribution graphically illustrated in the figure. The sequence repeats every 64 slot sets (128 opposed slots, and 256 slots in total).

Figure 18:
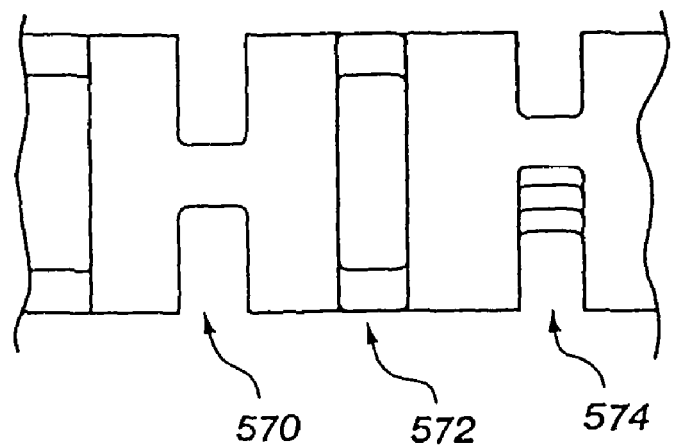
FIG. 18 shows a side view of a portion of a micromachined tube illustrating a slot orientation distribution in an exemplary embodiment.
Figure 19:
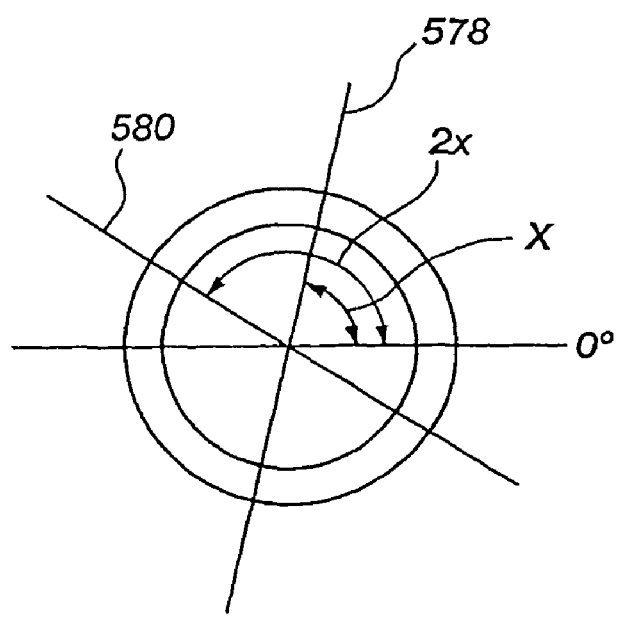
FIG. 19 shows a diagram further illustrating the slot set distribution shown in FIG. 18.

With reference to FIGS. 18 and 19, in another embodiment, the slot distribution may be defined by a helical pattern. With groups of two slots each, a first slot pair 570 may be at zero degrees. A second slot pair 572 may be rotated with respect to the first through a chosen angle x. For example, this angle can be 85 degrees. A third slot pair 574 may be oriented by rotation through an angle equal to 2x, or 170 degree in the exemplary embodiment. This pattern may be continued, as the next slot pair (not shown) may be oriented at 3x or 255 degrees, etc. continuing to turn, for example, in the same direction and by the same magnitude of angular rotation, x. The bending axis 576 formed by the first slot pair 570 may be oriented at 0 degrees; and the next bending axis 578 formed by the second slot pair may be oriented at 85 degrees in the example, and the third bending axis 580 at 170 degrees, and so on. This exemplary pattern will repeat after 72 slot pairs (144 total slots) where x may be equal to 85 degrees. The orientation of any pair of slots (and hence the bending axis) will be given by the following sequence: Pair 1=0 degrees;

Pair 2=x degrees; Pair 3=2x degrees; Pair N=(N−1)x degrees. Where the increment x may be 85 degrees, this may be equivalent to 0; 85; 170; 255; ... (N−1)85 ... degrees. This has been found to give good bending and torque transmission characteristics and low whip.

Thus, each longitudinally adjacent pair of slots may be rotated an angle around the axis from the previous pair, and the angle may be, for example, less than 89 degrees and greater than 31 degrees. In some such embodiments, the angle may be greater than 80 degrees (e.g., 85 degrees). In other embodiments, however, the angle may be in the range of 70-90 degrees and the average of the angles, computed over 10 adjacent sets of slots, may be less than 89 degrees and greater than 70 degrees. As an example, the angle may alternate between 90 degrees and 80 degrees, thus averaging 85 degrees. Other patterns satisfying this average would be apparent to a person of skill in the art. As also would also be apparent to a person skilled in the art, a 95 degree rotation is the same thing as an 85 degree rotation, but in the opposite direction Gust a change in the direction of the helix). Thus, in this situation and as used herein, a range of 31 to 89 degrees in the rotation angle between slots, for example, is the same as a range from 91 to 149 degrees. Similarly, a range of 70 to 90 degrees is the same as a range of 90 to 110 degrees.

Referring to FIGS. 16A-16D, in embodiments of slotted tube or body 514 having three slots 550 per group, adjacent groups of slots 550 may be rotated about the axis relative to each other by about 60 degrees. Thus, in general, adjacent groups may be rotated by an angle of 180 degrees divided by the number of slots 550 per group. In embodiments wherein the segments 546 form a helical pattern, the angle of rotation may be slightly different than the angle given by this formula. This slight difference may be, for example, more than zero or one degree, but less than ten degrees. For instance, this slight difference may be five degrees. Thus, in embodiments having three slots 550 per group, adjacent groups of slots 550 may be rotated about the axis by about 55 degrees relative to each other.

In another aspect, the micromachining pattern can be altered to provide preferred bending directions. This can be useful in customizing the guidewire to reach a target location within a particular anatomical structure, or even a particular individual patient. As an example of this, a MRI or CAT scan can produce a data set from which a preferred access route, for example vasculature to a target site, can be constructed in three dimensions. The guidewire can be micromachined to provide locally variable flexibility as needed to facilitate the traversing the last critical distance to the target site. A catheter individually customized for that patent may be made from that data set (for example sent to the manufacturer via the Internet) and shipped out to the user very rapidly, since micromachining may be a computer-controlled automated process that may be customized based on the data set in accordance with another automated procedure. This guidewire (or catheter) may be individually identified by a bar code as described herein.

The various embodiments of guidewires described above are examples of solid medical devices in accordance with the present invention. However, there are also embodiments of the present invention which are tubular. Examples of tubular embodiments are described next. As an example, the present invention also provides, in a particular embodiment, a catheter configured to navigate through anatomy. The catheter may have a tubular body with a proximal end, a distal end, and a longitudinal axis extending at least from the proximal end to the distal end. There may also be a plurality of groups or pairs of slots formed into the body, and each slot may be substantially perpendicular to the axis. Each slot in a pair may be on substantially opposite sides of the axis.

Figure 20:
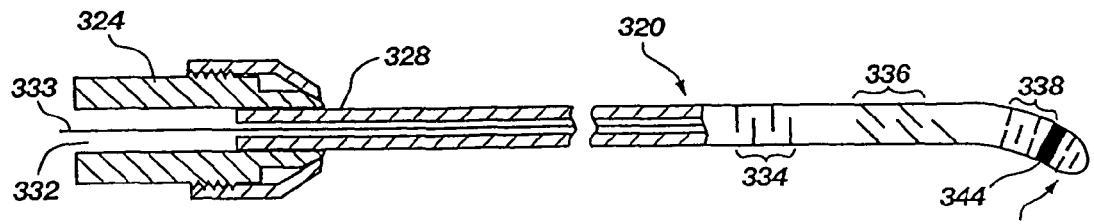
FIG. 20 is a side partially cross-sectional view of a tubular medical device formed in accordance with the present invention.

FIG. 20 is a side, partial, partially cross-sectional view of a tubular medical device 320 made in accordance with the present invention. Tubular medical devices in accordance with the present invention, such as medical device 320, may be, for example, guidewires or catheters, or may perform multiple or other functions. A re-positionable torquer or pin vise type torquing chuck 324 is shown attached to a proximal end 328. Chuck 324 may be detachable and may be configured to attach to the body and to facilitate manually rotating the body about the axis. The chuck 324 may include an opening, bore, or luer adapter 332, which may be, for example, configured to facilitate introduction of medications into the interior of the tubular medical device 320. The distal end 340 of the device may be curved to facilitate navigation through the anatomy. The tip at distal end 340 may be closed as shown in FIG. 20, or may be open. The tip may be rounded to minimize trauma to anatomy.

Figure 21A:
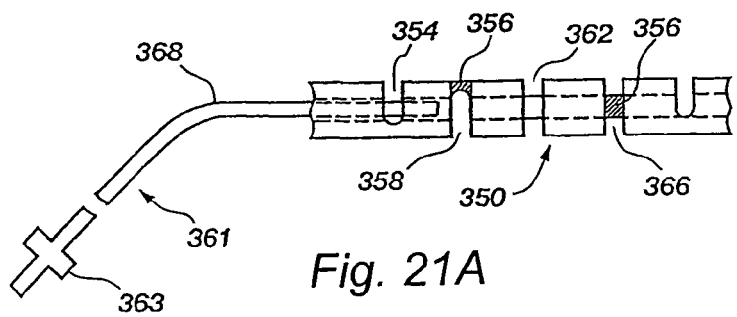
FIGS. 21A, 21B and 22 show side views of part of three embodiments of tubular medical devices in accordance with the present invention formed with slots substantially equally spaced around the axis and substantially perpendicular to the axis in accordance with principles of the present invention.

In some embodiments, a wire may be disposed inside the tubular body and may be slidable therein. The wire may have at least one bend formed in it, which may effect the shape of the device when the wire is inside, compared to when the wire is removed. The wire may also effect (e.g., increase) bending stiffness. An example of such an embodiment is illustrated in FIG. 21A. Wire or mandrel 361 may be insertable in the hollow of the tubular medical device 320. One purpose of such a wire mandrel or solutions may be, for example, to allow tracking location and/or movement of the medical device 320 as it is navigated in vasculature or body cavities. Wire mandrel 361 may be made radiopaque to facilitate X-ray fluoroscopy or, if magnetic resonance imaging (MRI) is used, the wire mandrel 361 may be made of a material active for MRI detection such as gadolinium or gadolinium compound, gadolinium encapsulated in a sheath, dysprosium, or dysprosium encapsulated in a sheath. Alternatively, a radiopaque solution may be introduced into the interior of the tubular medical device 320 or a solution visible in MRI may be used, in embodiments where MRI rather than X-ray fluoroscopy is utilized.

The wire mandrel 361 may also be used to change the curvature of the tubular medical device 320 as desired by the user. For example, the tubular medical device 320 may be formed with a portion of it curved or angled (such as the curved distal end 340) and a straight wire mandrel 361 may then be inserted into the medical device to straighten it out and then removed when desired to allow the medical device to resume the curved shape. Alternatively, the tubular medical device 320 may be formed to be straight and the wire mandrel 361 formed with selected curves so that when the mandrel is inserted into the tubular medical device, the mandrel would cause the medical device to assume a curved shape. In this embodiment, when the mandrel is removed, the medical device may again straighten. In this manner, depending upon the initial shape of the wire mandrel 361 and/or the tubular medical device 320, the shape of the medical device may be controlled to a certain extent while disposed in vasculature or body cavities.

The tubular medical device 320 may be constructed of nickel titanium alloy and may range in size from about 0.008 inches to 0.090 inches in outside diameter, and about 0.005 inches to 0.084 inches in inside diameter, and about 175 to 300 cm in length. The tubular medical device 320 may also be made of stainless steel, polymers, or other materials having suitable properties.

Slots, cuts, gaps or openings 334, 336, 338 or some combination thereof may be formed in the tubular medical device 320 along the length thereof, for example, by saw cutting (e.g., diamond grit embedded semiconductor dicing blade); electron discharge machining, laser cutting, or etching (for example using the etching process described in U.S. Pat. No. 5,106,455) to provide for bending flexibility of the medical device. Slots 334 may be generally perpendicular or crosswise to the long dimension of the medical device and may be formed on alternate sides of the medical device. In exemplary embodiment illustrated, slots 336 are angled, which may allow longer slots, and slots 338, on the distal end 340 of the medical device, are substantially perpendicular to the axis of the medical device.

In some tubular embodiments, the slots may form rings within the body of the medical device. This configuration may allow the slots and rings to provide for bending flexibility in the medical device, while maintaining torsional stiffness. By controlling and varying the spacing, depth and type of slots, the flexibility in bending and the torsional stiffness of the medical device may be selected. Generally, the more closely spaced the slots and the greater their depth, the more flexible in bending the medical device will be. In the preferred embodiment, the slots on the distal end of the medical device may be formed so as to allow a minimum bending radius of the distal tip of ½ inch or less. However, modification of the exact shape, orientation, and spacing of the slots will also allow selective modification or preservation of the torsional characteristics of the cross section at the distal end and at various locations along the tubular member somewhat independently of bending flexibility.

The distal end 340 of the medical device may be preshaped with a curve, as shown, to allow for directing the medical device around curves and bends. Advantageously, the tip may be rounded to minimize the chance of traumatic piercing of body tissue. Also formed on the distal end 340 may be a radiopaque or MRI marker or band 344. The band 344 may be gold or platinum alloy (for X-ray fluoroscopy) or gadolinium or dysprosium, or compounds thereof (for MRI), and may be formed on the distal end 340 by deposition, wrapping or use of the shape memory alloy (NiTi) effect to "lock" the band around the end. Alternatively, a radiopaque plug may be disposed in the lumen at the distal end 340 (or an MRI marker).

FIG. 21A is a side, partial view of a tubular medical device 350 formed with perpendicular slots 354, 358, 362, 366, etc., along the length thereof. In the exemplary embodiment illustrated, slot 354 is formed on the top of the medical device 350, slot 358 is formed on the bottom, slot 362 is formed on the near side of the medical device, and slot 366 is formed on the far side. Thus, each slot may be rotated, for example, by 180 degrees or 90 degrees, and offset from the preceding slot. The slots may be formed to provide preferential bending (flex) in one plane, or may be formed randomly or in some pattern to allow bending (flex) equally, non-preferentially, in all planes. This may be achieved, for example, by circumferentially spacing the slots.

The perpendicular slots in FIG. 21A create flexure segments 356 between the base of each slot and the opposing side of the tubular medical device. As may be envisioned by a skilled artisan, segments 356 may flex when medical device 350 bends or is loaded in torsion.

Figure 21B:
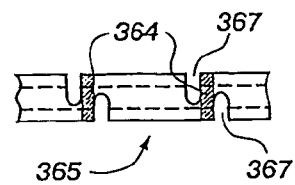

FIG. 21B is a side partial view of a tubular medical device 365 formed with pairs of slots 367 formed on opposite sides of the medical device and staggered or offset. These slots form rings 364 there between, and the segments of rings 364 between the slots may flex when medical device 365 is bent. The flexibility (bending stiffness), longitudinal strength, and torsional stiffness of the tubular medical device may be determined primarily by the dimensions and flexure properties of the segments formed by the slots: e.g., segments between opposing slots (such as segments 376, 423, 426, and 430 between slots 374, 424, 428, and 432, in FIGS. 22 and 24 respectively); and segments between adjacent offset slots or between slots and the side of the medical device (such as segments 356 and segments forming part of rings 364 in FIGS. 21A, and 21B respectively). Very flexible sections with opposed slots (such as shown in FIG. 22) generally require that the slots be deep and/or wide, to yield flexible beams 384.

Figure 22:
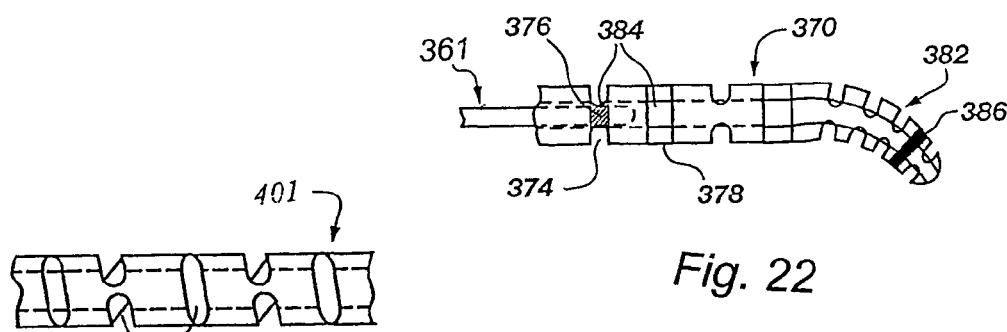

As illustrated in FIGS. 21A and 22, disposed in the tubular medical device 350 may be a solid wire mandrel 361 that may have a bend 368, which may cause the tubular medical device 350 to conform to bend 368, as previously discussed. The solid wire mandrel 361 may stiffen medical device 350, at least for that portion in which the mandrel is inserted. A stop 363 may be located at the proximal end of the mandrel 361 to prevent movement of the mandrel, and in particular the distal end of the mandrel, beyond a certain point in the medical device 350, for example, to avoid puncturing tissue beyond the distal end of the medical device by the distal end of the mandrel. Further, the mandrel 361 may be tapered at its distal end, and thus be more flexible at the distal end. Mandrel 361 may have a blunt or dulled tip.

FIG. 22 shows an exemplary embodiment of a tubular medical device, medical device 370, also with slots 374, 378, etc. formed therein. Distal end 382 of the medical device 370 may be curved, and may include a radiopaque or MRI band 386. In some embodiments, the distal ends of the medical devices are shapeable by the clinician by heating, bending, or both.

Figure 23A:
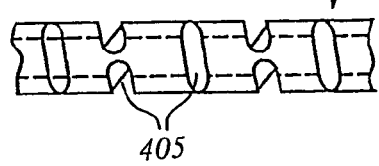
FIGS. 23A and 23B are side views of part of other embodiments of tubular medical devices in accordance with the present invention, where slots are not substantially perpendicular to the axis, in accordance with principles of the present invention.
Figure 23B:
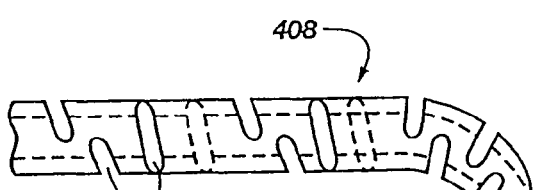

FIGS. 23A and 23B show side partial views of a tubular medical device 401 having opposed slots 405 formed at an angle other than perpendicular to the axis of medical devices 401 and 408.

Figure 24:
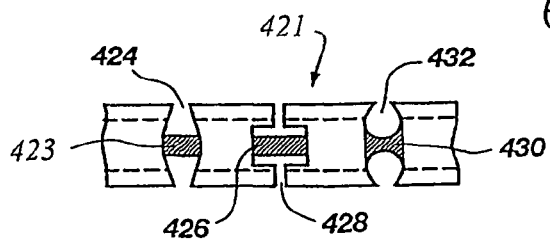
FIG. 24 is a side, partial view showing three different types of slots which may be utilized in a hollow medical device in accordance with the present invention.

In some tubular embodiments, at least some of the slots may have a cross sectional shape that may be, for example, square, rectangular, wedge-shaped, T-shaped, or substantially circular. FIG. 24 is a side, partial view of a tubular medical device 421, showing three alternative type slots 424, 428 and 432. These type slots may provide a built-in flexure stop to prevent further flexure of the medical device 421 when the slot openings close to contact one another and prevent further flexure in that direction. The slots 424 may be formed on opposite sides of the medical device 421 and may be wedge- or triangle-shaped, for example, with the greater width of the wedge being at the bottom of the slot. The slots 428 may be likewise formed on opposite sides of the medical device 421 in the form of T's, with the crosspiece of the T closest to the axis of the medical device. The slots 432 may be generally circular as shown. Other slot shapes may also be provided to meet the needs of the user. The slots 424, 428, and 432 are shown oppositely oriented, but it will be apparent that the slots may also be formed at circumferentially-spaced locations about the medical device, or at alternating locations such as shown and described with regard to other figures above.

All three types of slots shown in FIG. 24 form segments, shown in cross-hatch as areas 423, 426, and 430, respectively, between oppositely disposed slots. This configuration provides at least two distinct benefits. First, it allows the segment to be longer than the gap of the flexure stop. This may limit the amount of strain in the segment. This may be achieved, for example, by rotating adjacent pairs of slots by 45 degrees with respect to one another or some other selected angular amount.

Advantageously, longitudinally adjacent pairs of slots may be rotated about 90 degrees or other dimensional amounts around the medical device from one to another to provide flexure in bending. However, the slots may be located to provide preferential flexure in only one, two, three, etc. directions, if that is desired.

Figure 25:
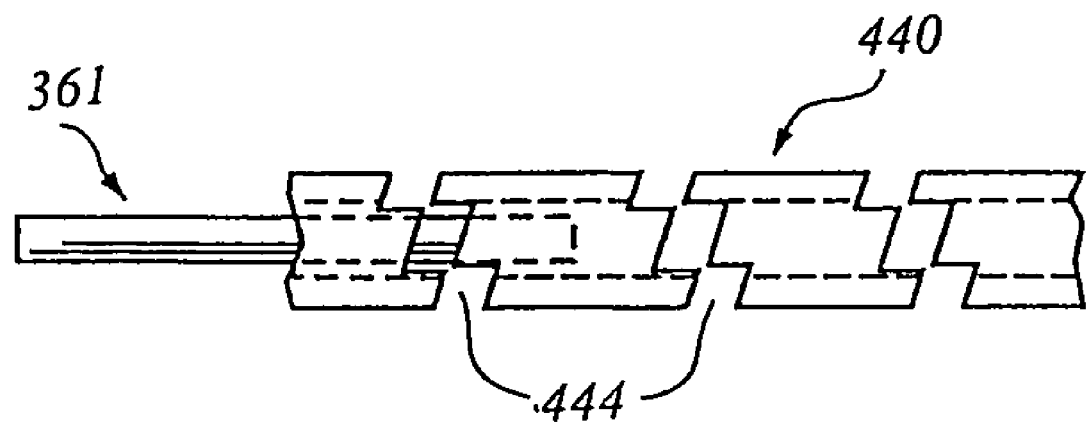
FIG. 25 is a side, partial view of still another embodiment of a tubular medical device with slots forming interlocking teeth, in accordance with the present invention.

FIG. 25 is a side, partial view of an alternate embodiment, tubular medical device 440 having slots 444 which may extend all the way through the medical device to separate it into pieces. The slots or etchings may be formed with teeth which interlock when the medical device is reassembled. When the medical device is inserted into a vasculature passageway, the teeth in the slots 444 may interlock to prevent relative rotation thereof and to transmit torque, but also allow significant lateral flexibility. Medical device 440 may include mandrel 361.

The tubular medical device disclosed may be used as a guide wire with a catheter threaded thereover in a conventional manner, or may be used, for example, to deliver medication to a target location in a manner similar to a catheter. With slots formed along the length or at least a portion of the length of the tubular medical devices, the medication may leak from the bore of the medical device out into the vasculature passageway. The location of discharge of medication from the tubular medical device may be controlled by controlling depth of the slots as well as the location thereof. In addition, a polymer sleeve may be inserted in the lumen or bore of a tubular medical device, on the outside, or both, for sealing and preventing the outflow or discharge of medication from the medical device lumen. The length of such sleeves on the medical device may determine the discharge points of medication from the medical device.

In addition, a stiffening mandrel or wire can be inserted through the bore or lumen of a tubular medical device as already discussed, and such mandrel or wire can be curved at selected locations such as location 368 in the mandrel 350 of FIG. 21A, to cause a corresponding bend in the tubular medical device. Alternatively, the tubular medical device can be formed with one or more bends and then a substantially straight mandrel may be inserted into the hollow of the medical device to cause it to straighten as needed. Also, the mandrel can be made of a material so that it may be visible either with X-ray fluoroscopy or MRI, depending upon the process used to view the clinical procedure.

Figure 26:
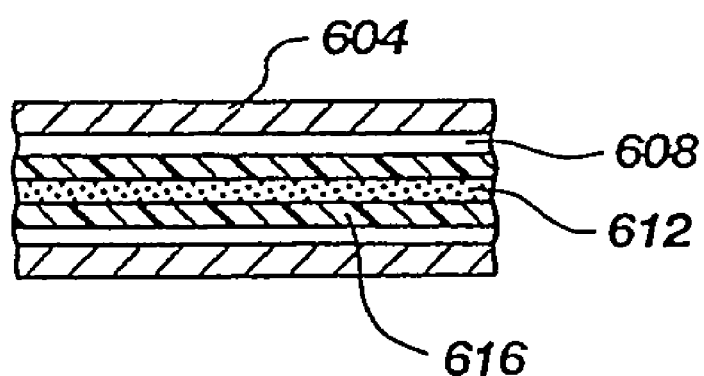

FIG. 26 is a side, cross-sectional, partial view of a tubular catheter medical device 604 made from a metallic or other electrically conductive alloy, in the lumen 608 of which may be disposed an electrically conductive wire 612 about which may be disposed an electrically insulative sheath 616. Alternatively, the interior wall of the lumen 608 may include a layer of insulation and obviate the need for the insulative sheath 616. For instance, the diameter of the lumen 608 may be 0.009 inches, and the diameter of the wire 612 and sheath 616 may be 0.006 inches.

Device 604 may be used, for example, for making internal electrical measurements such as the detection of voltage patterns at a target location in the body. Also, device 604 may be used for ablation in which a radio frequency or other signal may be transmitted over the conductor tube 604 and conductor wire 612 to the distal end to tissue in front of the distal end. In addition, a heating coil may be used with the device 604 at the distal end to provide a heating element for performing thermal treatment at a target location in the body. Also, other electrical measurements or treatments may be utilized with the structure shown in FIG. 26.

Figure 27:
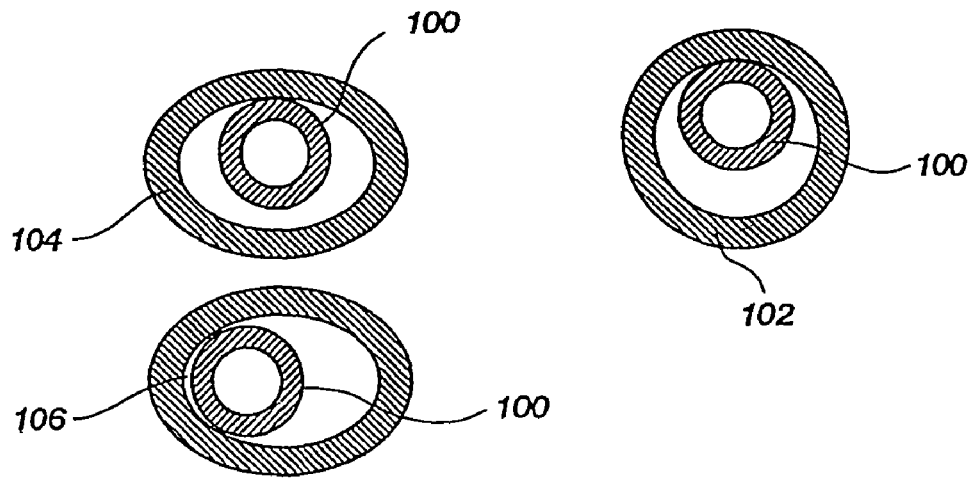
FIG. 27 shows cross-sectional views of guide wires disposed within the lumen of circular and elliptical catheters.

FIG. 27 shows cross-sectional views of tubular medical devices disposed within the lumen of circular and elliptical catheters. Solid medical devices are similar. As will be apparent, when a circular catheter is advanced into the vasculature of a patient and navigates curves and other tortuous routes, the cross-sectional shape of the catheter may flatten out in places into a more elliptical cross-section. When a medical device 100 is disposed in catheter 102 contact between device 100 and catheter 102 can only occur at one relatively flat location. However, with an elliptical catheter 104, the medical device 100 will typically not remain against a flat side. The medical device may push against the tight corner of the catheter lumen, and may wedge on nearly opposite sides as shown. In this condition, it can be seen that the normal forces between the medical device and the catheter may be much larger, resulting in larger frictional forces which may hinder the movement of the medical device within the catheter. Thus, in many embodiments, it is important that catheters maintain a circular cross section as much as possible.

Figure 28:
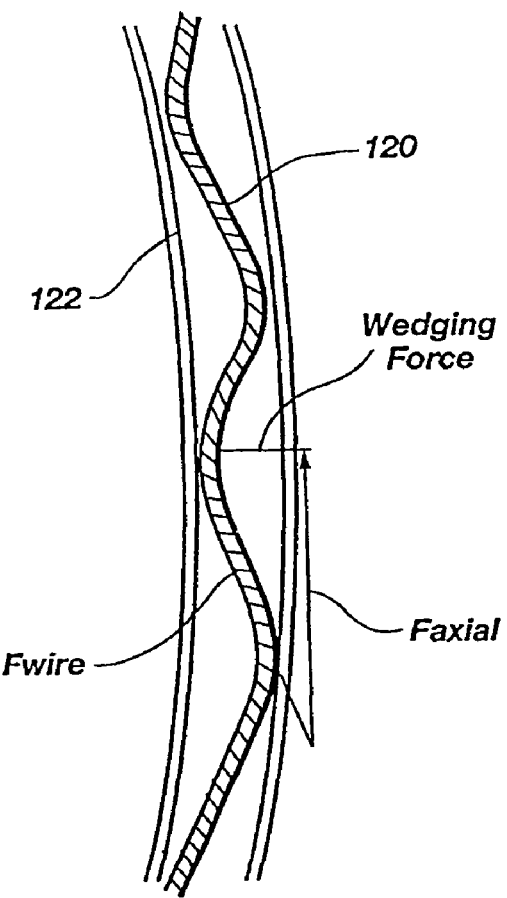
FIG. 28 shows the potential serpentine path of a guidewire through a catheter or other lumen where the guidewire is pushed, which tends to wedge the guide wire within the lumen.

FIG. 28 shows the potential serpentine path of a torqued medical device 120 through a catheter 122. When an axial driving force or pushing force (denoted Fwire in FIG. 28) is applied to the medical device 120, depending on the flexibility of the device in bending, the pushing force will be converted into an axial force (denoted Faxial) and a perpendicularly oriented wedging force (denoted Wedging Force) which may tend to jam the medical device within the catheter. Thus, in many embodiments of the present invention, it is important that the medical device not be too flexible in bending, especially at the proximal end where pushing forces will be greatest.

As mentioned above, slotted tubular medical devices such as micromachined catheters may have a sleeve or liner in many applications or embodiments, for example, to prevent fluid from escaping through the micromachined slots. Liners may provide other benefits in some embodiments, such as providing additional bending stiffness, reducing stress in the slotted tubular member, and the like. The following describes several embodiments for such liners, which are illustrated in FIGS. 29-37. Various liners in accordance with the present invention are in the form of tubular members, which may be used for applications other than as liners for slotted tubes or bodies. Such other uses may include, for example, as catheters, as an external covering for a slotted tube or body, as a conduit for a bodily or medical fluid, or the like, including uses where collapse or kink resistance, bending flexibility, or both, are desirable.

Accordingly, some exemplary embodiments of the present invention have a tubular polymer sleeve that may be coaxial with at least part of the body. For instance, the body may be tubular, and the sleeve may be inside the body or inside at least part of the body. The sleeve may prevent leakage of liquids through the slots, for example, if the device is used as a catheter to deliver medication to a particular location. In various embodiments, the sleeve may be slidably disposed with respect to the body, or may be attached to the body at one or more locations.

Figure 29:
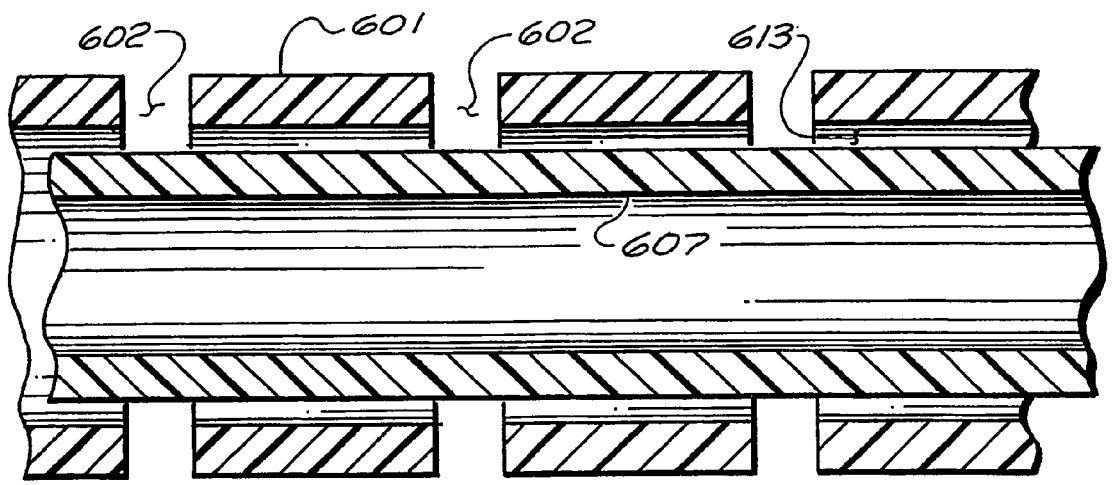
FIG. 29 is a side cross-sectional view of part of a slotted tubular body, for example, of a catheter, with a liner, which may be to prevent fluids from leaking through the slots, wherein there is space between the body and the liner to facilitate bending flexibility of the body.

Referring to FIG. 29, micromachined metal tubes (e.g., body or tube 601) may have a liner, for example, liner 607, which may cover slots 602 and may prevent fluid leakage through slots 602 in metal tube 601. The desired characteristics of liner 607 may be: high lateral flexibility, resistance to kinking, high hardness and lubricity of the lumen, high burst pressure, and minimal wall thickness. In some embodiments, it may be also beneficial to the performance of the device if the liner 607 is not in intimate contact with the inner wall of the metal tube. Thus, in the exemplary embodiment illustrated, annular space 613 exists between slotted tube 601 and liner 607.

In the embodiment illustrated in FIG. 29, liner 607 may need to have sufficient wall thickness that it will not kink or collapse when the medical device or catheter is bent in a tight radius. In other embodiments, thinner polymer liners may be bonded (e.g., with adhesive) to the slotted tube inner wall. But both bonded and thick-wall liners may stiffen the medical device or catheter so much that clinical performance may be degraded.

Thus, various embodiments of this invention provide a liner that can be extremely thin and flexible and yet not collapse when bent. Such liners may have an anti-collapsing structure, such as a coil, a braid, rings, one or more grooves, or a bellows or corrugated shape. The supported liner of the present invention may have a wall thickness, for example, as low as 0.0005" and not collapse on bending. This may be advantageous both from flexibility and catheter lumen maximization perspectives. Liner 607 may be bonded to slotted tube 601 at the proximal and distal ends, and in some embodiments in some intermediate points, without sacrificing the benefits of flexibility that this design provides.

Figure 30:
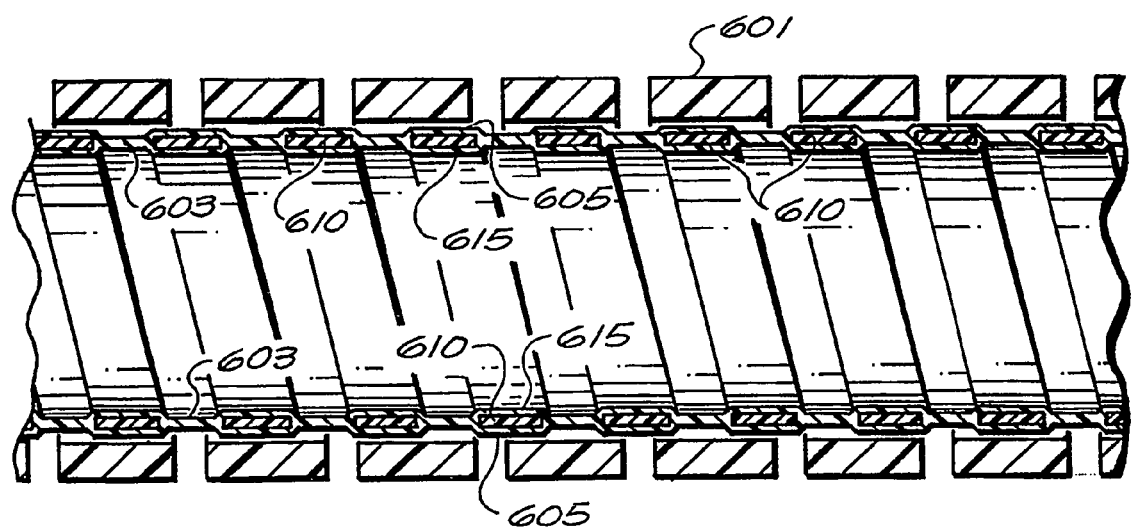
FIG. 30 is a side cross-sectional view of part of a slotted tubular body, for example, of a catheter, with a liner that has an embedded coil to act as an anti-collapsing structure and prevent collapsing of the liner.

In an exemplary embodiment of the present invention, FIG. 30 illustrates a slotted tubular body 601, for example, of a catheter, with a liner 603 that has an anti-collapsing structure that comprises embedded coil 610. Liner 603 is shown covering all of the slots shown, but in some embodiments, liner 603 may extend only part way through tubular body 601, and may cover only part of the slots therein. Liner 603 may comprise an outer polymer layer 605 and an inner polymer layer 615, and coil 610 may be located between the two polymer layers 605 and 615.

The liner shown in FIG. 30 may be manufactured by first forming or installing polymer tube 605 in slotted tube 601. For example, polymer tube 605 may be blown into slotted tube 601. Thus, polymer tube 605 may be in contact with the inner wall of slotted tube 601. The polymer may be, for example, polyethylene, PEBAX, HYTREL, or another suitable material. Blowing in tube 605 may involve using heat, pressure, or both to expand the polymer tube 605. Then coil 610 may be constrained on a mandrel and slid into the first polymer tube 605 and released. The coil 610 may have a memory position at a diameter greater than the bore of the first polymer tube 605 so coil 610 expands into contact with tube 605 when coil 610 is released. A second polymer tube 615 may then be blown, for example, into the bore of the coil 610. The coil 610 may thus be embedded between the polymer tubes 605 and 615, which may bond to each other where they touch between loops of the coil 610. Coil 610 may be made from metal or a polymeric material. In various embodiments, metals such as stainless steel, platinum, and nickel-titanium may be used or polymers such as nylon, polyester and polyimide may be used.

Figure 31:
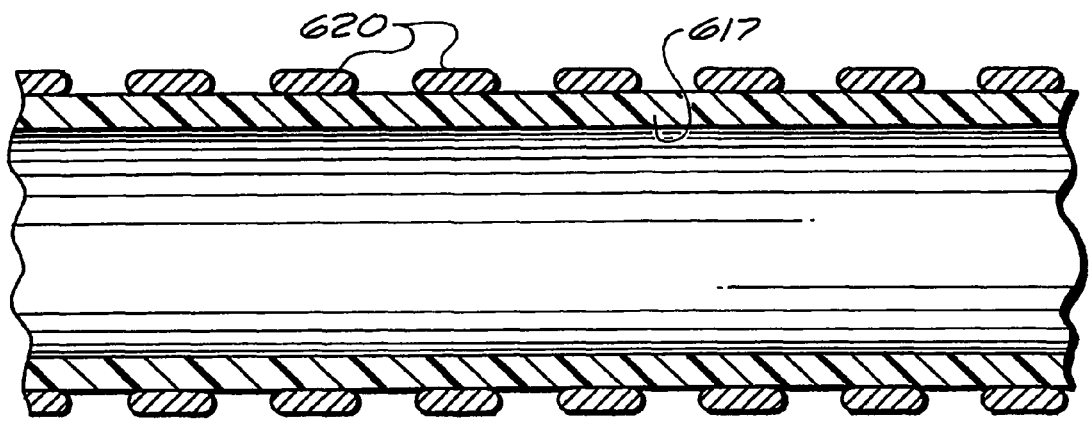
FIG. 31 is a side cross-sectional view of part of a liner configured with an external coil, braid, or annular rings, as an anti-collapsing structure.

FIG. 31 shows a polymer tubular member or liner 617 with external anti-collapsing structure 620. Anti-collapsing structure 620 may be annular in shape and comprise a plurality of rings, may be helical and form one or more coils, or may be a braid or a combination of such structures, for example. As used herein, annular means in the shape of a circle, a ring, or a right circular cylinder or sleeve, but when referring to an anti-collapsing structure, does not include a helical or spiral shape. A braid, for instance, may comprise a plurality of helical coils wound in opposite directions. In some embodiments, these helical coils may be connected or twisted together where they cross. The embodiment illustrated in FIG. 31 may be similar to the embodiment described with reference to FIG. 30, without the outer polymer tube or layer 605. The outer polymer layer 605 may be unnecessary in some applications, and space may be saved by omitting this layer.

Anti-collapsing structure 620 may be formed, for example, of round (circular or substantially circular cross section) or ribbon wire. As used herein, ribbon wire is wire with a cross section that has one dimension that is at least twice the perpendicular dimension. In some embodiments, ribbon wire may be used with a cross section that has one dimension that is at least 3 or 4 times the perpendicular dimension, or more. Ribbon wire may have a flat, rectangular, or oval cross section, for example, or may have the cross section shown for anti-collapsing structure 610 or 620 in FIG. 30 or 31.

An anti-collapsing structure 620 that is in the shape of a helical coil may provide flexibility and avoid the radial space consumed where the wires of a braid cross. On the other hand, braids may provide higher tensile strength, torsional stiffness, or both, and may provide additional alternatives for assembly of liner 617 and anti-collapsing structure 620. Another alternative embodiment of anti-collapsing structure 620 is a multiple-start helical coil, which may have multiple layers, alternating helix directions, or both. Alternating helix directions may provide added tensile strength, torsional stiffness, or both, but may have reduced bending flexibility.

The wire (of anti-collapsing structure 620, for example) can be made of a radiopaque material such as a platinum alloy, or other metals like stainless steel, or nitinol. In other embodiments, anti-collapsing structure 620 may be constructed from a rigid polymer such as nylon, polyester, polycarbonate, high density polyethylene, or polypropylene. The inner polymer tube or liner 617 can be made of polymers such as TEFLON, polyethylene, urethane, silicone, or various thermoplastic elastomers (TPE's). An exemplary embodiment uses a Nitinol ribbon coil anti-collapsing structure 620 with a ribbon thickness of 0.0006" and a width of 0.005" wound at a pitch of 0.009" over a PTFE tube 617 with a 0.021, outer diameter and a 0.001" wall thickness.

A coil or braid anti-collapsing structure 620 can be held against the outer wall of the polymer tube (liner 617) by spring action of the coil or braid or by a thin polymer coating such as parylene, urethane, silicone, or epoxy. Alternatively, the coil or braid anti-collapsing structure 620 can be constructed to fit around the polymer tube with minimal force between them to allow some relative motion between the layers for increased flexibility. Another alternative embodiment is to thermally fuse the anti-collapsing structure 620 to the polymer liner 617.

Figure 32:
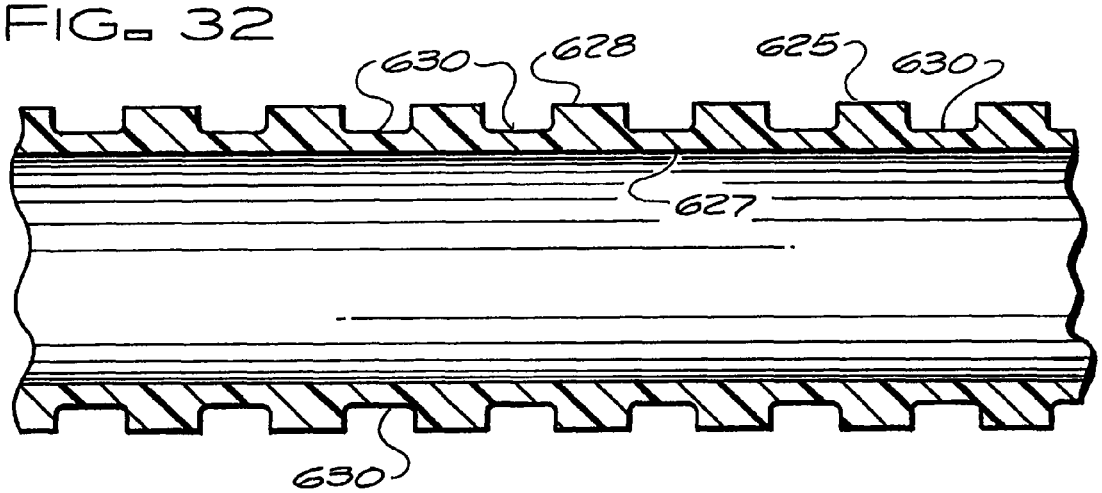
FIG. 32 is a side cross-sectional view of part of a liner configured with one or more grooves to act as an anti-collapsing structure and help prevent collapsing.
Figure 34:
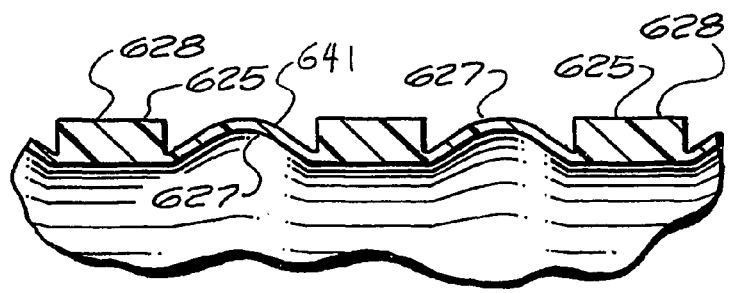
FIG. 34 is a cross-sectional detail view illustrating deformation of the thin area of the liner shown in FIG. 32.
Figure 33:
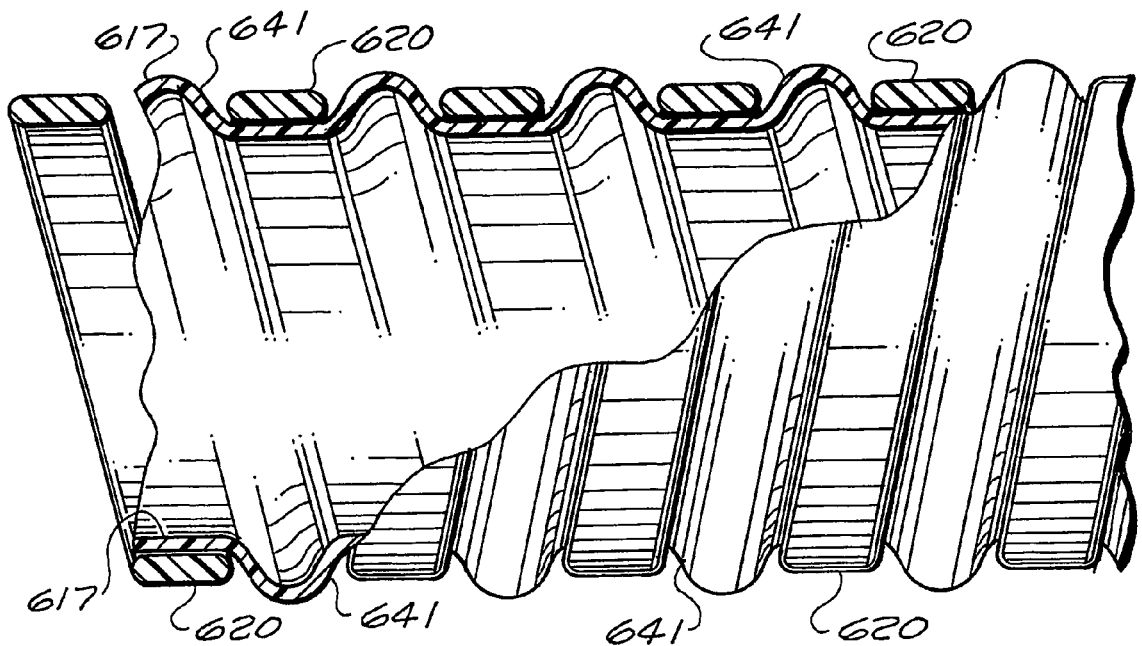
FIG. 33 is a side partially cross-sectional view illustrating a liner formed into corrugations extending outward between the loops of a helical anti-collapsing structure.

FIG. 32 is a cross-section illustrating a grooved polymer tube type of tubular member or liner 625. This embodiment may give higher flexibility and kink resistance without the additional components required for the anti-collapsing structure 620 embodiment described above. The polymer liner tube 625 may be grooved (with grooves 630) to provide thin areas 627 that may be flexible, and ridges or thick areas 628 that may be resistant to kinking and serve as an anti-collapsing structure. The construction can consist of a plurality of circular grooves 630 or it can comprise one or more continuous helical grooves 630, either single start or multi-start. This may result in multiple ring-like thick areas 628 or one or more helical thick areas 628. As used herein, either the thick areas 628 or the grooves 630 may be considered an anti-collapsing structure. Some embodiments may have both grooves 630, and a separate anti-collapsing structure (e.g., anti-collapsing structure 620), which may be located within grooves 630. For example, a coil anti-collapsing structure 620 may be fitted within a matching helical groove 630.

The grooves 630 may be made, for example, by grinding, machining, thermal forming or molding. Alternatively, the structure can be constructed by winding a coil of like material on the tube and thermally fusing them together. The width, depth, and spacing of the grooves 630 can be varied to optimize the characteristics of the tube (e.g., liner 625). An exemplary embodiment uses a single helical groove 630 with a depth of ¾ of the wall thickness, a width of approximately 1 wall thickness, and a pitch of approximately 2 wall thicknesses.

Figure 35:
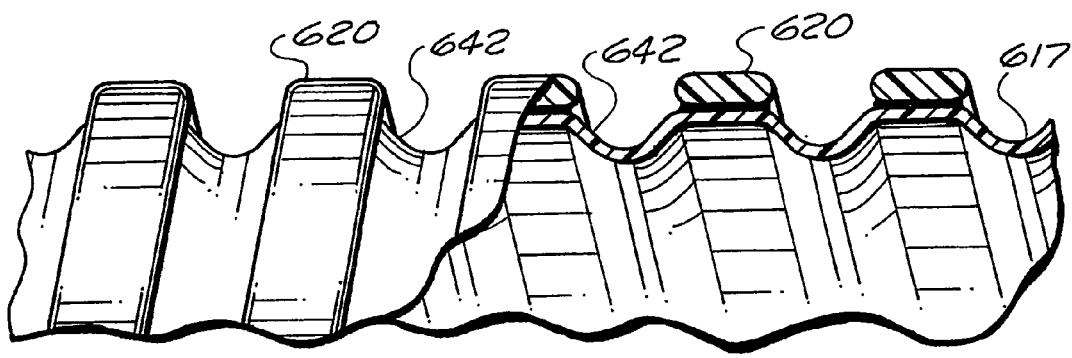
FIG. 35 is a partially cross-sectional detail view illustrating a liner formed into corrugations extending inward from a helical anti-collapsing structure.
Figure 36:
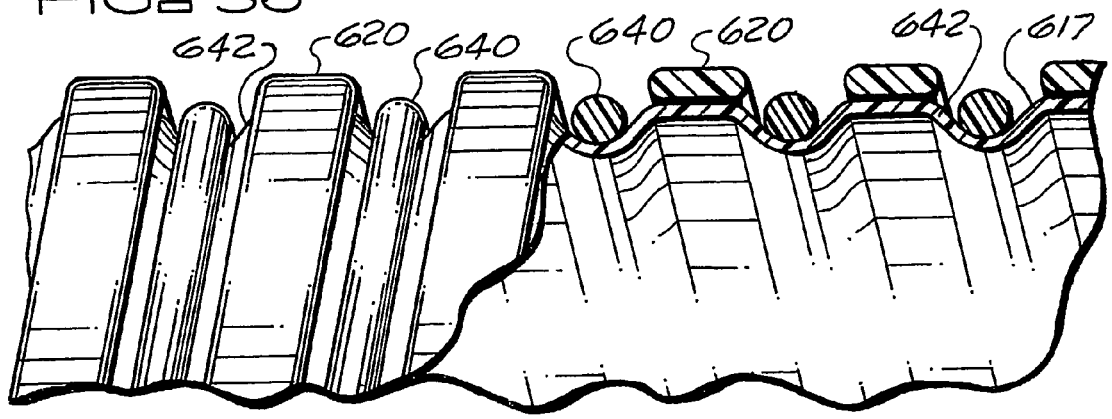
FIG. 36 is a partially cross-sectional detail view illustrating a liner formed into corrugations extending inward from a helical anti-collapsing structure, the inward corrugations being supported by a coil.

In some embodiments of the present invention, tubular member or liner 617, or thin areas 627, may be deformed into a corrugated shape or structure similar to a bellows as shown in FIGS. 33-36. In the exemplary embodiment shown in FIG. 33, for example, liner 617 has been placed inside anti-collapsing structure 620, and liner 617 has been deformed outward, in the radial direction, between windings or sections of anti-collapsing structure 620. Thus, liner 617 may form outward convolutions or corrugations 641. Similarly, thin area 627 is deformed in FIG. 34 forming outward corrugation 641. In FIGS. 35 and 36, liner 617 is bonded to anti-collapsing structure 620, and has been deformed inward, in the radial direction, forming inward convolutions or corrugations 642. In some embodiments, there may also be an outer polymer layer (e.g., tube or polymer layer 605 described above). Deformed thin areas 627 or corrugations 641 or 642 may be helical or annular, for example.

Corrugations 641 or 642 may be formed in tubular member or liner 617 and may constitute an anti-collapsing structure, or may be combined with a separate anti-collapsing structure such as anti-collapsing structure 620. Embodiments of the present invention having a deformed thin area 627 or corrugations 641 or 642 may be more flexible in bending than alternative embodiments. Such embodiments may also perform well at resisting collapsing or kinking. In embodiments having both corrugations and a separate anti-collapsing structure on the outside of liner 617, inward corrugations 642 may be more flexible than outward corrugations 641 for a given anti-collapsing structure 620 and liner 617. In addition, inward corrugations 642 and may allow a tighter bend radii in the embodiment illustrated because liner 617 does not interfere with approaching bands or loops of anti-collapsing structure 620 on the inside of the bend.

On the other hand, outward corrugations 641 generally do not encroach on the lumen in the embodiment illustrated as do inward corrugations 642. But other embodiments may have an anti-collapsing structure on the inside of the liner (e.g., anti-collapsing structure 615 shown in FIG. 30 inside layer 605 of liner 603). In such embodiments, inward corrugations may interfere with approaching loops of the anti-collapsing structure. Corrugations may also be formed in liners having two layers (e.g., layers 605 and 615 shown in FIG. 30), in which case either inward or outward corrugations may interfere with approaching loops of the anti-collapsing structure.

Outward corrugations 641 may be formed by applying heat, internal pressure, or both, to a tube 617 which is supported or surrounded concentrically by ant-collapsing structure 620. In such a process, the wall thickness of tube or liner 617 may become thinner as corrugation 641 is formed. Outward corrugations 641 may also be formed by compressing liner 617 (e.g., in the axial direction), which may be in combination with heat, internal pressure, or both. Outward corrugations 641 may also be formed with a mold having circular or helical corrugations, for example. Such a method may be used, for example, for embodiments not having a separate ant-collapsing structure such as anti-collapsing structure 620. Molding may also involve applying heat, internal pressure, or both. In embodiments using a mold, anti-collapsing structure 620 may be omitted, may be installed after molding, or may be installed on liner 617 before corrugations 641 are formed. Outward corrugations 641 may also be formed by installing anti-collapsing structure 620 onto liner 617 where the diameter of anti-collapsing structure 620 is less than that of liner 617. Heat may also be applied to soften liner 617.

Inward corrugations 642 may be formed, for example, by stretching tube or liner 617 (with anti-collapsing structure 620 located thereon) while hot, cooling liner 617, and then compressing liner 617 in the axial direction while applying heat at a lower temperature than used during the stretching operation. This method may be used for a liner 617 made of PTFE, for example. The use of a lower temperature during compression may avoid recovery of the stretch or elongation imparted to liner 617 during the stretching operation. Methods of forming inward corrugations 642 may involve applying external pressure to liner 617 while liner 617 is bonded to or supported by anti-collapsing structure 620. External pressure may be used in addition to or in lieu of compression in the axial direction.

In another embodiment of the present invention illustrated in FIG. 36, a helical anti-collapsing structure 620 may be attached to (shown), placed inside, or formed on liner 617, and then a smaller diameter coil 640 (i.e., smaller coil diameter) may be wound onto liner 617 between windings of anti-collapsing structure 620 forming inward corrugations 642. External pressure, compression in the axial direction, heat, or a combination thereof, may be used in addition to coil 640.

As described herein, many embodiments of the present invention may have a bending stiffness that is not constant along its length, but varies along its length. As an example, the bending stiffness may decrease from the proximal end to the distal end. In some embodiments, the bending stiffness of the liner may vary accordingly. Variations in bending stiffness along tubular member or liner 617 may be gradual along part or all of its length, or may occur in one or more increments. Such variations in bending stiffness may be accomplished by varying the wall thickness of liner 617, varying the shape of the corrugations (e.g., 641 or 642), or both. As used herein, the corrugated shape of tubular member 617 includes the dimension in the axial direction, the dimension in the radial direction, and whether the corrugation extends inward or outward from the anti-collapsing structure 620. In some embodiments, varying of the wall thickness of liner 617 may be accomplished by varying the amount of stretching of liner 617 when forming corrugations 641 or 642, for example. Thus, the wall thickness of liner 617 and the shape of corrugations 641 or 642 may be interrelated or combined.

In one exemplary embodiment, more heat may be applied at the distal end during formation of the corrugations (e.g., 641 or 642). This heat may soften tubular member or liner 617 more at that location causing it to deform more due to tension or pressure that is applied. Thus, although an equal tension or pressure may be applied along liner 617, the corrugations (e.g., 641 or 642) may be more pronounced (i.e., greater in radial dimension) at the distal end, which may also stretch liner 617 more at that location and result in a thinner wall thickness. As a result, liner 617 may be more flexible at its distal end due to a differing corrugated shape, thinner wall thickness, or both.

In some embodiments, corrugations 641 or 642 may be formed in the distal end, but not in the proximal end, or may be more pronounced in the distal direction. This may be accomplished with a mold, and formation of a thinner wall thickness may accompany formation of more pronounced corrugations, for example, outward corrugations 641.

In addition, or in the alternative, in some embodiments of the present invention, the pitch of anti-collapsing structure 620 may be varied along the length of tubular member or liner 617 to vary the bending stiffness of tubular member 617. For instance, the pitch of anti-collapsing structure 620 may be greater at the distal end, providing larger corrugations 641 or 642 at that location in liner 617 as compared to the proximal end. In an exemplary embodiment, anti-collapsing structure 620 may be initially formed with a greater pitch at the distal end. In some embodiments, anti-collapsing structure 620 may then be installed on or bonded to liner 617. Then pressure may be applied. Heat may also be applied during application of the pressure. The larger distal portions of liner 617 between sections or loops of anti-collapsing structure 620 may deform more as a result of the pressure than the smaller proximal portions of liner 617. This may result in corrugations 641 or 642 with greater dimension and thinner wall thickness at the distal end, resulting in lower bending stiffness at that location, in comparison with the proximal end.

In another embodiment, anti-collapsing structure 620 may initially have a continuous pitch along its length, and may be bonded in this condition to liner 617, or formed thereon. Then liner 617 and anti-collapsing structure 620 may be stretched at the distal end resulting in a larger pitch of anti-collapsing structure 620 and a thinner wall thickness of liner 617 at that location in comparison to the proximal end, for example. Then pressure may be applied resulting in corrugations 641 or 642 that are more pronounced and have a thinner wall thickness at the distal end. Heat may be applied during the stretching, application of the pressure, or both, and may be applied in varying amounts along liner 617.

In still another embodiment, anti-collapsing structure 620 may initially have a smaller pitch at its distal end, and may be bonded in this condition to liner 617, or formed thereon. Then liner 617 and anti-collapsing structure 620 may be stretched at the distal end resulting in a larger pitch of anti-collapsing structure 620 and a thinner wall thickness of liner 617 at that location, in comparison to before the stretching occurred. In various embodiments, the pitch at the distal end of anti-collapsing structure 620 may remain less than at the proximal end, may become about the same, or may become larger than the pitch at the proximal end. Then pressure may be applied resulting in corrugations 641 or 642 that have a thinner wall thickness and may be more pronounced (e.g., have a greater radial dimension) at the distal end. Again, heat may be applied during the stretching, application of the pressure, or both.

Further, some embodiments may transition from outward corrugations 641 at the proximal end or at an intermediate location to inward corrugations 642 at the distal end. Such an embodiment may allow a tighter bend radius at the distal end as well as providing less bending stiffness at that location.

In various embodiments of the present invention, anti-collapsing structure 620 may be bonded to the outer (shown) or inner surface of liner 617, for example, with epoxy. In some embodiments, anti-collapsing structure 620 may be embedded, fully or partially, within liner 617. Liner 617 may be composed of different types of material, which may be polymers, for example, a PTFE inner layer and an elastomeric outer layer (e.g., PEBAX). The lumen of any of these liner structures may be coated with a lubricious coating such as a hydrophilic coating.

One embodiment of this invention has a polymer liner tube that may be grooved only near the distal end of the device where increased flexibility may be required or desired. The size range of various exemplary embodiments may be lumen diameters ranging from 0.012" to 0.1" and liner wall thickness ranging from 0.0005" to 0.015".

Referring once again to FIG. 29, various embodiments of the present invention involve Liner Fixation. Generally, liner 607 constructions may need to be anchored to the outer slotted NiTi tube 601 to achieve a working device. The liners 607 may, for example, be bonded to the metal tube 601 at the proximal and distal ends. Intermediate anchor points may also be provided, and may, inter alia, transfer tensile loads, torsional loads, or both from the metal tube 601 to the liner structure 607. These intermediate points may be located, for example, at the proximal end of the slotted portion of metal tube 601 and at the midpoint of the slotted portion of metal tube 601.

It is to be understood that the above-described exemplary embodiments and arrangements are only illustrative of the application of the principles of the present invention. Numerous modifications and alternative arrangements may be devised by those skilled in the art without departing from the spirit and scope of the present invention and the appended claims may be intended to cover such modifications and arrangements.

What is claimed is:

1. A medical device, comprising:
   an elongate tubular member having a plurality of slots formed therein;
   a liner disposed within the tubular member, the liner having an outer surface and a plurality of corrugations formed along the outer surface, wherein at least some of the plurality of corrugations are disposed at longitudinal positions along the medical device substantially corresponding to longitudinal positions of at least some of the plurality of slots; and
   a coil disposed along the outer surface of the liner.

2. The medical device of claim 1, wherein the corrugations include outward corrugations.

3. The medical device of claim 1, wherein the corrugations include inward corrugations.

4. The medical device of claim 3, further comprising a second coil disposed in the inward corrugations.

5. The medical device of claim 1, wherein the coil is a ribbon coil.

6. The medical device of claim 1, further comprising a polymeric member disposed over the coil and the liner.

7. The medical device of claim 1, wherein the tubular member has a longitudinal axis, wherein at least some of the plurality of slots are arranged in groups that are disposed at the same location along the longitudinal axis of the tubular member, and wherein at least some of the groups include three slots.

8. The medical device of claim 7, wherein the groups of slots include a first group at a first position along the longitudinal axis of the tubular member and a second group adjacent the first group at a second position along the longitudinal axis of the tubular member, and wherein the second group is rotated relative to the first group.

9. The medical device of claim 8, wherein the second group is rotated by an angle greater than 50 degrees and less than 70 degrees relative to the first group.

10. The medical device of claim 9, wherein the second group is rotated by an angle of about 55 degrees relative to the first group.

11. A medical device, comprising:
    an elongate tubular member having a plurality of slots formed therein;
    a liner disposed within the tubular member, the liner having an outer surface and a plurality of inward corrugations formed along the outer surface, wherein at least some of the plurality of inward corrugations are disposed at longitudinal positions along the medical device substantially corresponding to longitudinal positions of at least some of the plurality of slots; and
    an anti-collapsing structure disposed along the outer surface of the liner.

12. The medical device of claim 11, wherein the anti-collapsing structure includes a coil.

13. The medical device of claim 12, wherein the coil is a ribbon coil.

14. The medical device of claim 11, further comprising a coil disposed in the inward corrugations.

15. The medical device of claim 14, further comprising a polymeric member disposed over the coil and the anti-collapsing structure.

* * * * *

UNITED STATES PATENT AND TRADEMARK OFFICE
CERTIFICATE OF CORRECTION

| | | |
|---|---|---|
| PATENT NO. | : 7,914,466 B2 | Page 1 of 1 |
| APPLICATION NO. | : 10/523709 | |
| DATED | : March 29, 2011 | |
| INVENTOR(S) | : Clark C. Davis et al. | |

It is certified that error appears in the above-identified patent and that said Letters Patent is hereby corrected as shown below:

Column 18
    Line 59, delete "Gust", and insert therefor -- (just --.

Signed and Sealed this
Twenty-fourth Day of May, 2011

David J. Kappos
*Director of the United States Patent and Trademark Office*